United States Patent
Desaulniers et al.

(10) Patent No.: US 10,724,036 B2
(45) Date of Patent: Jul. 28, 2020

(54) SYSTEM AND METHOD FOR REVERSIBLE PHOTO-CONTROLLED GENE SILENCING

(71) Applicant: University of Ontario Institute of Technology, Oshawa (CA)

(72) Inventors: Jean-Paul Desaulniers, Whitby (CA); Matthew Hammill, Cobourg (CA)

(73) Assignee: University of Ontario Institute of Technology, Oshwa, Ontario (CA)

( * ) Notice: Subject to any disclaimer, the term of this patent is extended or adjusted under 35 U.S.C. 154(b) by 232 days.

(21) Appl. No.: 15/992,707

(22) Filed: May 30, 2018

(65) Prior Publication Data

US 2018/0346909 A1   Dec. 6, 2018

Related U.S. Application Data

(60) Provisional application No. 62/512,319, filed on May 30, 2017.

(51) Int. Cl.

| | | |
|---|---|---|
| *C12N 15/113* | (2010.01) | |
| *A61K 31/7125* | (2006.01) | |
| *A61K 31/713* | (2006.01) | |
| *A61K 31/5517* | (2006.01) | |
| *A61K 47/16* | (2006.01) | |
| *A61K 41/00* | (2020.01) | |
| *C12N 15/11* | (2006.01) | |

(52) U.S. Cl.
CPC ........ *C12N 15/113* (2013.01); *A61K 31/5517* (2013.01); *A61K 31/7125* (2013.01); *A61K 41/0042* (2013.01); *A61K 41/0057* (2013.01); *A61K 47/16* (2013.01); *C12N 15/111* (2013.01); *C12N 2310/14* (2013.01); *C12N 2310/318* (2013.01); *C12N 2320/50* (2013.01)

(58) Field of Classification Search
None
See application file for complete search history.

(56) References Cited

PUBLICATIONS

Yamana et al. Bioorganic & Medicinal Chemistry 1999, vol. 7, pp. 2977-2983.*
Braasch, D. A.; Jensen, S.; Liu, Y.; Kaur, K.; Arar, K.; White, M. A.; Corey, D. R., RNA interference in mammalian cells by chemically-modified RNA. Biochemistry 2003, 42 (26), 7967-75.
Selvam, C.; Mutisya, D.; Prakash, S.; Ranganna, K.; Thilagavathi, R., Therapeutic potential of chemically modified siRNA: Recent trends. Chem Biol Drug Des 2017, 90(5): 665-678.
Lee, S. H.; Kang, Y. Y.; Jang, H. E.; Mok, H., Current preclinical small interfering RNA (siRNA)-based conjugate systems for RNA therapeutics. Adv Drug Deliv Rev 2016, 104, 78-92.
Corey, D. R., Chemical modification: the key to clinical application of RNA interference? Journal of Clinical Investigation 2007, 117 (12), 3615-3622.
Kitamura, Y., Synthesis of Nucleic Acid Mimics and Their Application in Nucleic Acid-based Medicine. Yakugaku zasshi : Journal of the Pharmaceutical Society of Japan 2016, 136 (11), 1491-1499.
Young, S. W.; Stenzel, M.; Yang, J. L., Nanoparticle-siRNA: A potential cancer therapy? Critical reviews in oncology/hematology 2016, 98, 159-69.
Mikat, V.; Heckel, A., Light-dependent RNA interference with nucleobase-caged siRNAs. RNA (New York, N.Y.) 2007, 13 (12), 2341-7.
Shah, S.; Rangarajan, S.; Friedman, S. H., Light-activated RNA interference. Angewandte Chemie (International ed. in English) 2005, 44 (9), 1328-32.
Beharry, A. A.; Woolley, G. A., Azobenzene photoswitches for biomolecules. Chem Soc Rev 2011, 40 (8), 4422-37.
Lubbe, A. S.; Szymanski, W.; Feringa, B. L., Recent developments in reversible photoregulation of oligonucleotide structure and function. Chem Soc Rev 2017, 46 (4), 1052-1079.
Kashida, H.; Fujii, T.; Asanuma, H., Threoninol as a scaffold of dyes (threoninolnucleotide) and their stable interstrand clustering in duplexes. Org Biomol Chem 2008, 6 (16), 2892-9.
Goldau, T.; Murayama, K.; Brieke, C.; Asanuma, H.; Heckel, A., Azobenzene CNucleosides for Photocontrolled Hybridization of DNA at Room Temperature. Chemistry (Weinheim an der Bergstrasse, Germany) 2015, 21 (49), 17870-6.
Wu, L.; He, Y.; Tang, X., Photoregulating RNA digestion using azobenzene linked dumbbell antisense oligodeoxynucleotides. Bioconjug Chem 2015, 26 (6), 1070-1079.
Desaulniers, J.-P.; Hagen, G.; Anderson, J.; McKim, C.; Roberts, B., Effective gene-silencing of siRNAs that contain functionalized spacer linkages within the central region. RSC Advances 2017, 7 (6), 3450-3454.
Efthymiou, T. C.; Peel, B.; Huynh, V.; Desaulniers, J. P., Evaluation of siRNAs that contain internal variable-length spacer linkages. Bioorganic & Medicinal Chemistry Letters 2012, 22 (17), 5590-5594.
Jeno, Y.; Watanabe, Y.; Shibata, A.; Yoshikawa, K.; Takano, T.; Kohara, M.; Kitade, Y., Synthesis of nuclease-resistant siRNAs possessing universal overhangs. Bioorg Med Chem 2009, 17 (5), 1974-81.
Kitamura, Y.; Masegi, Y.; Ogawa, S.; Nakashima, R.; Akao, Y.; Ueno, Y.; Kitade, Y., Chemically modified siRNAs and miRNAs bearing urea/thiourea-bridged aromatic compounds at their 3'-end for RNAi therapy. Bioorg Med Chem 2013, 21 (15), 4494-501.

(Continued)

*Primary Examiner* — Tracy Vivlemore
(74) *Attorney, Agent, or Firm* — Bereskin & Parr LLP; Tony Orsi; Ainslie Parsons

(57) ABSTRACT

In one aspect, a chemically-modified siRNA for reversible photo-controlled gene silencing is provided. In one embodiment, one or more nucleotides the sense strand of the siRNA are replaced with a spacer comprising an azobenzene or derivative thereof. The azobenzene or derivative thereof undergoes isomerization between the trans-configuration and the cis-configuration in the presence of light from a light source and the siRNA optionally has higher RNA silencing activity when the azobenzene or derivative thereof is in the trans-configuration compared to the cis-configuration. In other aspects, the chemically-modified siRNAs may, for example, be useful as both therapeutics and research tools.

20 Claims, 11 Drawing Sheets
Specification includes a Sequence Listing.

(56) References Cited

PUBLICATIONS

Efthymiou, T. C.; Vanthi, H.; Oentoro, J.; Peel, B.; Desaulniers, J.-P., Efficient synthesis and cell-based silencing activity of siRNAS that contain triazole backbone linkages. Bioorganic & Medicinal Chemistry Letters 2012, 22 (4), 1722-1726.

Collingwood, M. A.; Rose, S. D.; Huang, L. Y.; Hillier, C.; Amarzguioui, M.; Wiiger, M. T.; Soifer, H. S.; Rossi, J. J.; Behlke, M. A., Chemical modification patterns compatible with high potency Dicer-substrate small interfering RNAs. Oligonucleotides 2008, 18, 187-199.

Desaulniers, J.P., Hammill, M. and Hagen G., Photochemical Control of siRNAs, 100th Canadian Chemistry Conference and Exhibition, Abstract published May 26, 2017.

* cited by examiner

SEQUENCE LISTING

```
<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: Synthetic construct

<400> SEQUENCE: 1
cuuacgcuga guacuucgat t                                                    21

<210> SEQ ID NO 2
<211> LENGTH: 21
<212> TYPE: DNA
<213> ORGANISM: Artificial Sequence
<220> FEATURE:
<223> OTHER INFORMATION: Synthetic construct

<400> SEQUENCE: 2
ttgaaugcga cucaugaagc u                                                    21

<210> SEQ ID NO 3
<211> LENGTH: 20
<212> TYPE: DNA
<213> ORGANISM: Artificial Sequence
<220> FEATURE:
<223> OTHER INFORMATION: Synthetic construct
```

```
<220> FEATURE:
<221> NAME/KEY: misc_feature
<222> LOCATION: (9)..(9)
<223> OTHER INFORMATION: n is an azobenzene derivative synthesized from
      4-nitrobenzyl alcohol

<400> SEQUENCE: 3
cuuacgcung uacuucgatt                                                     20

<210> SEQ ID NO 4
<211> LENGTH: 21
<212> TYPE: DNA
<213> ORGANISM: Artificial Sequence
<220> FEATURE:
<223> OTHER INFORMATION: Synthetic construct

<400> SEQUENCE: 4
ttgaaugcga cucaugaagc u                                                   21

<210> SEQ ID NO 5
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (20)..(20)
<223> OTHER INFORMATION: n is an azobenzene derivative synthesized from
      4-nitrobenzyl alcohol

<400> SEQUENCE: 5
cuuacgcuga guacuucgan                                                     20

<210> SEQ ID NO 6
<211> LENGTH: 21
<212> TYPE: DNA
<213> ORGANISM: Artificial Sequence
<220> FEATURE:
<223> OTHER INFORMATION: Synthetic construct

<400> SEQUENCE: 6
ttgaaugcga cucaugaagc u                                                   21

<210> SEQ ID NO 7
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: n is an azobenzene derivative synthesized from
      4-nitrophenethyl alcohol

<400> SEQUENCE: 7
cuuacgcnag uacuucgatt                                                     20

<210> SEQ ID NO 8
<211> LENGTH: 21
<212> TYPE: DNA
<213> ORGANISM: Artificial Sequence
<220> FEATURE:
<223> OTHER INFORMATION: Synthetic construct

<400> SEQUENCE: 8
ttgaaugcga cucaugaagc u                                                   21
```

```
<210> SEQ ID NO 9
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (9)..(9)
<223> OTHER INFORMATION: n is an azobenzene derivative synthesized from
      4-nitrophenethyl alcohol

<400> SEQUENCE: 9
cuuacgcung uacuucgatt                                                   20

<210> SEQ ID NO 10
<211> LENGTH: 21
<212> TYPE: DNA
<213> ORGANISM: Artificial Sequence
<220> FEATURE:
<223> OTHER INFORMATION: Synthetic construct

<400> SEQUENCE: 10
ttgaaugcga cucaugaagc u                                                 21

<210> SEQ ID NO 11
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (10)..(10)
<223> OTHER INFORMATION: n is an azobenzene derivative synthesized from
      4-nitrophenethyl alcohol

<400> SEQUENCE: 11
cuuacgcugn uacuucgatt                                                   20

<210> SEQ ID NO 12
<211> LENGTH: 21
<212> TYPE: DNA
<213> ORGANISM: Artificial Sequence
<220> FEATURE:
<223> OTHER INFORMATION: Synthetic construct

<400> SEQUENCE: 12
ttgaaugcga cucaugaagc u                                                 21

<210> SEQ ID NO 13
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (11)..(11)
<223> OTHER INFORMATION: n is an azobenzene derivative synthesized
      from 4-nitrophenethyl alcohol

<400> SEQUENCE: 13
cuuacgcuga nacuucgatt                                                   20

<210> SEQ ID NO 14
<211> LENGTH: 21
<212> TYPE: DNA
<213> ORGANISM: Artificial Sequence
```

```
<220> FEATURE:
<223> OTHER INFORMATION: Synthetic construct

<400> SEQUENCE: 14
ttgaaugcga cucaugaagc u                                              21

<210> SEQ ID NO 15
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (20)..(20)
<223> OTHER INFORMATION: n is an azobenzene derivative synthesized from
      4-nitrophenethyl alcohol

<400> SEQUENCE: 15
cuuacgcuga guacuucgan                                                20

<210> SEQ ID NO 16
<211> LENGTH: 21
<212> TYPE: DNA
<213> ORGANISM: Artificial Sequence
<220> FEATURE:
<223> OTHER INFORMATION: Synthetic construct

<400> SEQUENCE: 16
ttgaaugcga cucaugaagc u                                              21
```

SYSTEM AND METHOD FOR REVERSIBLE PHOTO-CONTROLLED GENE SILENCING

CROSS REFERENCE TO RELATED APPLICATION

This disclosure claims the benefit of U.S. provisional application No. 62/512,319, filed May 30, 2017, which is incorporated herein by reference in its entirety.

INCORPORATION OF SEQUENCE LISTING

A computer readable form of the Sequence Listing "21704-P53045US01_SequenceListing.txt" (8,192 bytes), submitted via EFS-WEB and created on May 29, 2018, is herein incorporated by reference.

FIELD

The present disclosure relates to chemically-modified siRNA molecules and methods of use thereof. In particular, the disclosure relates to reversible photo-controlled siRNA.

BACKGROUND

Short interfering RNAs (siRNAs) are used to induce gene silencing. They are a class of biological molecules that have the potential to be next generation therapeutics (Braasch et al, 2003). However, due to issues related to delivery, stability, and off-target effects, siRNAs still require some forms of chemical modification to make them appealing pharmaceutical candidates (Selvam et al, 2017; Lee et al, 2016).

Several chemical modifications have been explored to overcome many of the issues associated with structure (Corey et al, 2007; Kitamura et al, 2016). In addition, many different packaging systems have been utilized and studied to assist in localizing the siRNA to the correct tissue (Young et al, 2016). Despite advances, several issues still exist, notably off-target effects, i.e. tissue specific targeting. In order to reduce off-target effects and potentially activate an RNA at the desired target, methods that turn the siRNA on or off are desired.

SUMMARY

The present disclosure describes chemically-modified siRNAs containing azobenzene derivative spacers within the central region of the sense strand. Azobenzene is a compound that can photoisomerize between cis and trans isomers. The inventors have replaced two siRNA nucleotides with azobenzene and showed that azobenzene is successfully accommodated within the backbone of the siRNA as measured by dose-dependent knockdown of firefly luciferase. In addition to its RNAi biocompatibility, the inventors were able to photochemically control the activity of the modified siRNAs. The inventors demonstrated that it is possible to both inactivate and reactivate the modified siRNAs with ultraviolet and visible light, respectively. The inventors also synthesized a tetrachlorinated azobenzene derivative and showed that the isomerization of this derivative changes from trans to cis when exposed to green or red light and then is restored back to trans when exposed to blue or violet light.

Accordingly, in one aspect, in at least one embodiment, the present disclosure provides a chemically-modified siRNA molecule, wherein one or more nucleosides of a strand of the siRNA are replaced with a spacer comprising an azobenzene or a derivative thereof.

In one embodiment, the one or more nucleotides the spacer replaces are located in the sense strand of the siRNA.

In another embodiment, two nucleotides of the strand are replaced by the spacer comprising the azobenzene or derivative thereof.

In another embodiment, the spacer comprising the azobenzene or the derivative thereof is a compound of Formula I:

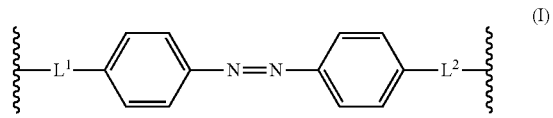

wherein
$L^1$ and $L^2$ are each independently a linker moiety; and
one or more available hydrogen atoms on the phenyl rings is optionally replaced with another group.

In another embodiment, $L^1$ and $L^2$ are each independently $C_{1-6}$alkylene, optionally wherein $L^1$ and $L^2$ are each methylene or ethylene.

In another embodiment, none of the available hydrogen atoms on the phenyl rings is replaced with another group.

In another embodiment, the azobenzene or derivative thereof undergoes isomerization from the trans-configuration to the cis-configuration in the presence of UV light.

In another embodiment, the azobenzene or derivative thereof undergoes isomerization from the cis-configuration to the trans-configuration in the presence of visible light.

In a further embodiment, the isomerization from the trans-configuration to the cis-configuration is reversible in the presence of visible light.

In a further embodiment, the isomerization from the cis-configuration to the trans-configuration is reversible in the presence of UV light.

In another embodiment, the one or more available hydrogen atoms in the ortho position on the phenyl rings is replaced with a halogen, optionally chlorine.

In a further embodiment, the azobenzene or derivative thereof undergoes isomerization from the trans-configuration to the cis-configuration in the presence of green and/or red light.

In a further embodiment, the azobenzene or derivative thereof undergoes isomerization from the cis-configuration to the trans-configuration in the presence of blue and/or violet light.

In another embodiment, the siRNA has higher RNA silencing activity when the azobenzene or derivative thereof is in the trans-configuration compared to the cis-configuration.

In another embodiment, the spacer comprising the azobenzene or derivative thereof is located within a central region of the siRNA. Optionally, the spacer comprising the azobenzene or derivative thereof is located at least 5 nucleotides away from the 3' end of the strand and at least 5 nucleotides away from the 5' end of the strand.

In another embodiment, the spacer comprising the azobenzene or derivative thereof is located between positions 9 and 12 of the strand nucleotides.

In another embodiment, the siRNA is directed to an oncogene.

In another aspect, in at least one embodiment, the present disclosure provides a method of activating and/or inactivating an siRNA molecule comprising:

(a) providing a chemically-modified siRNA wherein one or more nucleotides of a strand of the siRNA are replaced with a spacer comprising an azobenzene or derivative thereof, and (b) exposing the siRNA to light from a light source, wherein the azobenzene or derivative thereof undergoes isomerization between the cis-configuration and the trans-configuration upon exposure to the light and wherein the chemically-modified siRNA has higher RNA silencing activity when the azobenzene or derivative thereof is in the trans-configuration compared to the cis-configuration.

In one embodiment, the light is UV light and the azobenzene or derivative thereof undergoes isomerization from the trans-configuration to the cis-configuration upon exposure to the UV light.

In another embodiment, the light is visible light and the azobenzene or derivative thereof undergoes isomerization from the cis-configuration to the trans-configuration upon exposure to the visible light.

In another embodiment, the light is green and/or red light and the azobenzene or derivative thereof undergoes isomerization from the trans-configuration to the cis-configuration upon exposure to the green and/or red light.

In another embodiment, the light is blue and/or violet light and the azobenzene or derivative thereof undergoes isomerization from the cis-configuration to the trans-configuration upon exposure to the blue and/or violet light.

In another embodiment, the method further comprises introducing the chemically-modified siRNA to a cell.

In another embodiment, the chemically-modified siRNA is exposed to the light source prior to introducing the siRNA to the cell. Alternatively, in another embodiment, the chemically-modified siRNA is exposed to the light source after introducing the chemically-modified siRNA to the cell.

In another embodiment, the cell is a bacterial cell, a fungal cell, a plant cell or a mammalian cell.

In another aspect, in at least one embodiment, the present disclosure provides a method of reversibly silencing gene expression comprising:

(a) providing a cell with a chemically-modified siRNA directed to a gene in the cell, wherein one or more nucleotides of a strand of the siRNA are replaced with a spacer comprising an azobenzene or derivative thereof, and (b) exposing the cell to light from a light source that modulates the cis-trans isomerism of the azobenzene or derivative thereof.

In another embodiment, expression of the gene is decreased when the azobenzene or derivative thereof is in the trans-configuration.

In another embodiment, expression of the gene is lower when the azobenzene or derivative thereof is in the trans-configuration compared to the cis-configuration.

In another embodiment, the azobenzene or derivative thereof undergoes isomerization from the cis-configuration to the trans-configuration upon exposure to visible light.

In another embodiment, the azobenzene or derivative thereof undergoes isomerization from the trans-configuration to the cis-configuration upon exposure to UV light.

In another embodiment, the azobenzene or derivative thereof undergoes isomerization from the cis-configuration to the trans-configuration upon exposure to green and/or red light.

In another embodiment, the azobenzene or derivative thereof undergoes isomerization from the trans-configuration to the cis-configuration upon exposure to blue and/or violet light.

In another aspect, in at least one embodiment, the present disclosure provides a use of the chemically-modified siRNA as described herein for reversibly silencing gene expression.

In another aspect, in at least one embodiment, the present disclosure provides a use of the chemically-modified siRNA as described herein as a research tool.

In another aspect, in at least one embodiment, the present disclosure provides a use of the chemically-modified siRNA as described herein for treating a disease associated with increased or aberrant expression of a gene, wherein the siRNA is directed to the gene.

In another aspect, in at least one embodiment, the present disclosure provides a use of the chemically-modified siRNA as described herein for treating cancer.

In another aspect, in at least one embodiment, the present disclosure provides a method of treating a disease associated with increased or aberrant expression of a gene, comprising administering the chemically-modified siRNA as described herein to a mammal or cell in need thereof, wherein the chemically-modified siRNA is directed to the gene.

In another aspect, in at least one embodiment, the present disclosure provides a method of treating cancer, comprising administering the chemically-modified siRNA as described herein to a mammal or cell in need thereof.

Other features and advantages of the present disclosure will become apparent from the following detailed description. It should be understood, however, that the detailed description and the specific Examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

DETAILED DESCRIPTION

Figure 1:
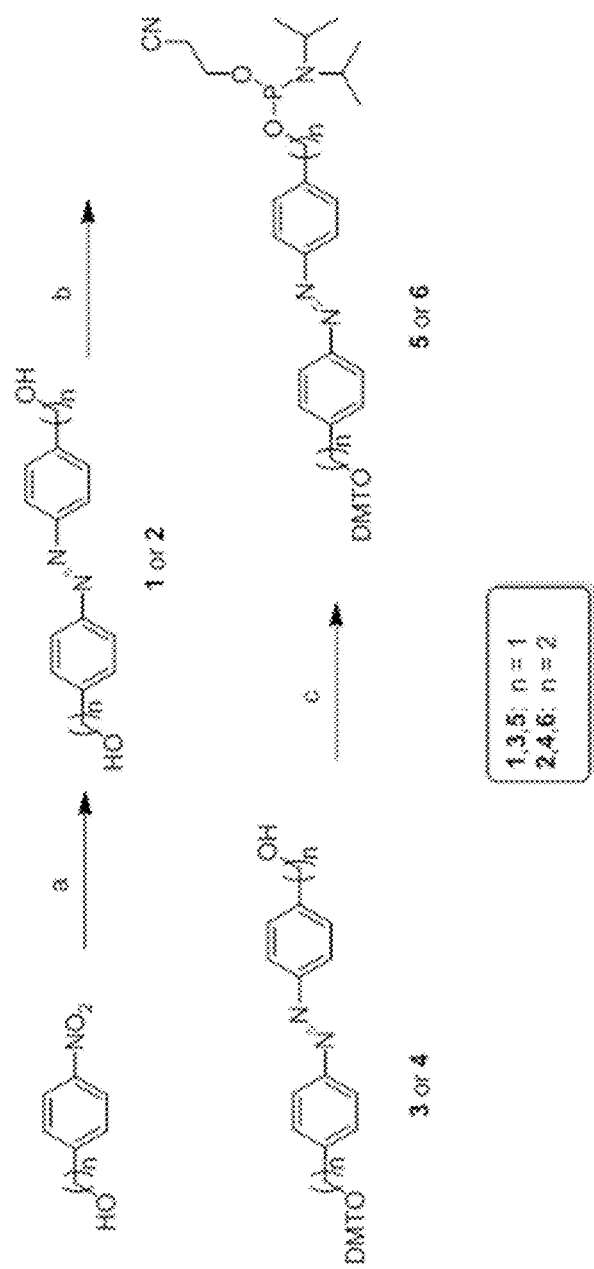
FIG. 1 shows the synthesis of azobenzene phosphoramidites: Synthesis of azobenzene phosphoramidites: (a) 4 equiv. of Zn and 8 equiv. of NaOH, $H_2O$, reflux overnight, 70% (1 and 4); (b) 1 equiv. dimethoxytrityl chloride (DMT-Cl), 3 equiv. TEA, THF, r.t., 35% (2 and 5); (c) 3 equiv. of 2-cyanoethyl N,N-diisopropylchlorophosphoramidite, 10 equiv. TEA, anh. DCM:ACN (1:1), r.t. 3 h, 63% (3) and 33% (6).

In one aspect, the present disclosure describes a short interfering RNA (siRNA) that incorporates an azobenzene moiety into the central region of the sense strand. This modification allows control of the activity of the siRNA via UV or visible light for inactivation or activation, respectively.

Compositions of Matter

Chemically-Modified siRNA

Accordingly, the disclosure provides a chemically-modified siRNA wherein one or more nucleotides of a strand of the siRNA are replaced with a spacer comprising an azobenzene or a derivative thereof.

As used herein, the term "siRNA" or "siRNA oligomer" or "siRNA molecule" and the like means a nucleic acid molecule capable of mediating RNAi (RNA interference). siRNAs are well known in the art. They are a class of double-stranded RNA molecules which interfere with the expression of specific genes with complementary nucleotide sequences by degrading mRNA after transcription, resulting in no translation.

Azobenzene is an organic compound composed of two phenyl rings linked by an N=N double bond. Of relevance to the present disclosure is the photoisomerization of the trans and cis isomers of azobenzene. The two isomers can be switched with particular wavelengths of light: ultraviolet light, which corresponds to the energy gap of the π-π* (S2 state) transition, for trans-to-cis conversion, and visible light, which is equivalent to that of the n-π* (S1 state) transition, for cis-to-trans isomerization. The cis isomer is less stable than the trans (for instance, it has a distorted configuration and is less delocalized than the trans configuration).

As used herein, "derivatives" of azobenzene refer to compounds having the core azobenzene structure of two phenyl rings linked by an N=N double bond in which one or more available hydrogen atoms on the phenyl rings is replaced with another group. Derivatives of azobenene contemplated herein have similar photoisomerization properties as azobenzene i.e. they are capable of being photoisomerized between the trans and cis isomers.

The term "available", as in "available hydrogen atoms" as used herein refers to hydrogen atoms that would be known to a person skilled in the art to be capable of replacement by a suitable group using methods known in the art.

It will be appreciated by a person skilled in the art that replacement of available hydrogen atoms on the phenyl rings of azobenzene by certain groups such as an electron donating group (EDG) or an electron withdrawing group (EWG) may adjust the wavelengths of light at which the azobenzene photoisomerizes. Accordingly, in an embodiment, the group replacing the one or more available hydrogen atoms is an electron withdrawing group or an electron donating group. In another embodiment, the group is an electron withdrawing group. In a further embodiment, the group is an electron donating group.

The term "electron donating group" or "EDG" as used herein refers to an atom or functional group that donates some of its electron density into a conjugated π system, thereby making the π system more nucleophilic. In some embodiments, the electron donating group is a tertiary amine.

The term "electron withdrawing group" or "EWG" as used herein refers to an atom or functional group that removes electron density from a conjugated π system, thereby making the π system more electrophilic. In some embodiments the electron withdrawing group is halo.

As used herein, the term "antisense strand" refers to the strand of an siRNA which includes a region that is substantially complementary or complementary to a target sequence. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of an siRNA that includes a region that is substantially complementary or complementary to a region of the antisense strand.

In an embodiment, the one or more nucleotides the spacer comprising the azobenzene or derivative thereof replaces are located in the sense strand of the siRNA.

There are examples in the literature where certain areas of the anti-sense strand function with a chemical modification. Accordingly, in another embodiment, the spacer is located in the anti-sense strand of the siRNA. In a further embodiment, the spacer is located in the anti-sense strand of the siRNA such that the spacer does not interfere with the ability of the siRNA to be integrated into the RNA-induced silencing complex (RISC). Accordingly, in another embodiment, the one or more nucleotides the spacer comprising the azobenzene or derivative thereof replaces are located in the antisense strand of the siRNA. In another embodiment, each of the strands of the siRNA comprises a spacer comprising the azobenzene or derivative thereof replacing one or more nucleotides.

In another embodiment, the spacer comprising the azobenzene or derivative thereof is located at the 3' or 5' end of the sense or antisense strand of the siRNA. In preferred embodiments, the spacer comprising the azobenzene or derivative thereof is located in the central region of the siRNA. As used herein, the term "central region of the siRNA" refers to the span of nucleotides positioned at least 5 nucleotides away from the 3' end of the sense or antisense strand and at least 5 nucleotides away from the 5' end of the sense or antisense strand. For example, in one embodiment, the spacer comprising the azobenzene or derivative thereof is located between nucleotides 8 and 13, optionally nucleotides 9 and 12 of the sense or antisense strand.

In an embodiment, the spacer comprising the azobenzene or derivative thereof replaces 1-2 nucleotides in the strand. In another embodiment, the spacer comprising the azobenzene or derivative thereof replaces 2 nucleotides in the strand. In an embodiment, the chemically-modified siRNA has one spacer comprising the azobenzene or derivative thereof. In alternative embodiments, the chemically-modified siRNA has more than one, for example 2 spacers comprising the azobenzene or derivative thereof.

It will be appreciated by a person skilled in the art that the spacer comprising the azobenzene or derivative thereof is linked to the remainder of the siRNA through any suitable means. In an embodiment, the spacer comprising the azobenzene or derivative thereof is linked to the remainder of the siRNA via a phosphodiester bond. Synthetic methods for forming bonds such as the phosphodiester bond are known and the selection of a suitable method for a particular spacer and linkage can be made by a person skilled in the art.

In an embodiment, the azobenzene or derivative thereof is linked to the remainder of the siRNA via a phosphodiester bond and the linkage is achieved through standard dimethoxytrityl-phosphoramidite chemistry. It will be appreciated by a person skilled in the art that in such a method, the spacer comprising the azobenzene or the derivative thereof is introduced via a precursor having an —OH moiety at each end; one to be protected by an acid-labile 4,4'-dimethoxytrityl (DMT) group and the other for the phosphoramidite moiety. It will also be appreciated by a person skilled in the art that in the case of azobenzene derivatives, any functional groups present which are reactive under the conditions for the dimethoxytrityl-phosphoramidite chemistry are protected by attaching a suitable protecting group then deprotected by suitable means upon The terms "protecting" and "protected" as used herein refers to using a chemical moiety, i.e. a "protecting group" of "PG" which protects or masks a reactive portion of a molecule to prevent side reactions in that reactive portion of the molecule, while manipulating or reacting a different portion of the molecule. After the manipulation or reaction is complete, the protecting group is removed under conditions that do not degrade or decompose the remaining portions of the molecule; i.e. the protected reactive portion of the molecule is "deprotected". The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3rd Edition, 1999 and in Kocienski, P. Protecting Groups, 3rd Edition, 2003, Georg Thieme Verlag (The Americas). Examples of suitable protecting groups include, but are not limited to t-Boc, $C_{1-6}$acyl, Ac, Ts, Ms, silyl ethers such as TMS, TBDMS, TBDPS, Tf, Ns, Bn, Fmoc, dimethoxytrityl, methoxyethoxymethyl ether, methoxymethyl ether, pivaloyl, p-methoxybenzyl ether, tetrahydropyranyl, trityl, ethoxyethyl ethers, carbobenzyloxy, benzoyl, methyl, triisopropylsilane triflyl, thiophenyl, cyclic protecting groups such as those comprising —$C(CH_3)_2$— and the like.

t-Boc as used herein refers to the group t-butyloxycarbonyl.

The term "acyl" as used herein, whether it is used alone or as part of another group, means straight or branched chain, saturated acyl groups. The number of carbon atoms that are possible in the referenced acyl group are indicated by the numerical prefix "$C_{n1-n2}$". For example, the term $C_{1-6}$acyl means an acyl group having 1, 2, 3, 4, 5 or 6 carbon atoms.

Ac as used herein refers to the group acetyl.

Ts (tosyl) as used herein refers to the group p-toluenesulfonyl.

Ms as used herein refers to the group methanesulfonyl.

TMS as used herein refers to the group trimethylsilyl.

TBDMS as used herein refers to the group t-butyldimethylsilyl.

TBDPS as used herein refers to the group t-butyldiphenylsilyl.

Tf as used herein refers to the group trifluoromethanesulfonyl.

Ns as used herein refers to the group naphthalene sulphonyl.

Bn as used herein refers to the group benzyl.

Fmoc as used herein refers to the group fluorenylmethoxycarbonyl.

In an embodiment, the precursor for the spacer comprising the azobenzene or derivative thereof is 2-cyanoethyl-4-O-{[4-hydroxyethyl-4'-O-(4,4'dimethoxytrityl)-O-methyl-diazenyl]}-N, N'-diisopropylaminophosphoramidite or 2-cyanoethyl-4-O-{[4-hydroxymethyl-4'-O-(4,4'dimethoxytrityl)-O-methyl-diazenyl]}-N, N'-diisopropylaminophosphoramidite.

In an embodiment, the spacer comprising the azobenzene or the derivative thereof is a compound of Formula I:

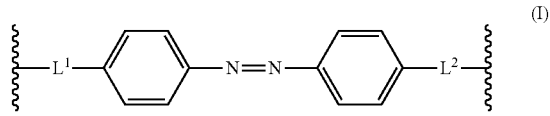

(I)

wherein $L^1$ and $L^2$ are each independently a linker moiety; and
one or more available hydrogen atoms on the phenyl rings is optionally replaced with another group.

In one embodiment, one or more available hydrogen atoms in the ortho position on the phenyl rings is optionally replaced with another group.

The linker moiety can be any suitable linker moiety. The term "linker moiety" as used herein refers to any molecular structure that joins two or more other molecular structures together. In an embodiment, $L^1$ and $L^2$ are each independently $C_{1-6}$alkylene.

In another embodiment, $L^1$ and $L^2$ are each independently $C_{1-4}$alkylene. In a further embodiment, $L^1$ and $L^2$ are each methylene. It is an embodiment that $L^1$ and $L^2$ are each ethylene.

The term "alkylene" as used herein, whether it is used alone or as part of another group, means straight or branched chain, saturated alkylene group, that is, a saturated carbon chain that contains substituents on two of its ends. The number of carbon atoms that are possible in the referenced alkylene group are indicated by the numerical prefix "$C_{n1-n2}$". For example, the term $C_{1-6}$alkylene means an alkylene group having 1, 2, 3, 4, 5 or 6 carbon atoms.

In an embodiment, the group replacing the one or more available hydrogen atoms on the phenyl rings is an electron withdrawing group. In another embodiment, the electron withdrawing group is halo.

The term "halo" as used herein refers to a halogen atom and includes F, Cl, Br and I.

In a further embodiment, the group replacing the one or more available hydrogen atoms is a nitro group.

In one embodiment, the group replacing the one or more available hydrogen atoms on the phenyl rings is chlorine. In another embodiment, the group replacing the one or more available hydrogen atoms on the phenyl rings is Br, F, I, —OMe, -OEt, —$NH_2$, —$SO_2$, —$NO_2$.

In an embodiment, the group replacing the one or more available hydrogen atoms on the phenyl rings is an electron donating group. In another embodiment, the electron donating group is a tertiary amine. In a further embodiment, the electron donating group has the structure —$NR^{2a}R^{2b}$, wherein $R^{2a}$ and $R^{2b}$ are each independently selected from $C_{1-4}$alkyl or $R^{2a}$ and $R^{2b}$, together with the nitrogen to which they are attached, form a nitrogen-containing heterocycloalkyl ring. In an embodiment, $R^{2a}$ and $R^{2b}$ are each ethyl. In another embodiment, $R^{2a}$ and $R^{2b}$, together with the nitrogen to which they are attached, form pyrrolidinyl, piperidinyl or N-methylpiperazinyl. In another embodiment, none of the available hydrogen atoms on the phenyl rings is replaced.

The term "nitrogen-containing heterocycloalkyl ring" as used herein, whether it is used alone or as part of another group, refers to a cyclic group containing 3 to 20 atoms, optionally 3 to 10 atoms, preferably 5 or 6 atoms, and at least one non-aromatic ring in which one of the atoms in that ring is nitrogen and one or more other atoms in the ring are optionally a heteromoiety selected from O, S, S(O), $SO_2$, N, NH and $NC_{1-4}$alkyl. Heterocycloalkyl rings are either saturated or unsaturated (i.e. contain one or more double bonds) and contain one or more than one ring (i.e. are polycyclic). When a heterocycloalkyl ring contains more than one ring, the rings may be fused, bridged, spirofused or linked by a bond.

Optionally, the group or groups replacing the one or more available hydrogen atoms on the phenyl rings are in one or both of the ortho positions on the phenyl rings.

In an embodiment, the chemically-modified siRNA is one or more of the chemically-modified siRNAs in Table 1.

Also contemplated within the disclosure are siRNAs comprising two or more spacers comprising an azobenzene or a derivative thereof. Indeed, researchers have successfully inserted more than one azobenzene into their oligonucleotides (Wu et al, 2015; Lubbe et al, 2017). In one embodiment, the sense strand comprises at least one spacer comprising an azobenzene or a derivative thereof and the antisense strand also comprises at least one spacer comprising an azobenzene or a derivative thereof.

Methods for the preparation of siRNAs are known to a person skilled in the art. For example, siRNAs may be produced by chemical synthesis. In an embodiment, the chemical synthesis is carried out in a method which comprises using an automated oligonucleotide synthesizer. Alternatively, RNA-containing portions of the siRNA may be prepared through transcription driven by RNA polymerase promotors. For example, vectors that express siRNAs within mammalian cells typically use an RNA polymerase III promoter to drive expression of a short hairpin RNA that mimics the structure of an siRNA.

siRNA molecules are commonly about 15 to 30 or 18 to 25 base pairs in length. In one embodiment, the siRNA includes an overhang at the 3' end of the sense and anti-sense strands. Common overhangs include dTdT or UU overhangs. In another embodiment, the siRNA includes "blunt ends", meaning that there are no unpaired nucleotides at the end of the siRNA, i.e., no nucleotide overhang.

The sequence of the siRNA molecule is complementary, or substantially complementary, to the gene to be silenced, or a portion thereof. An siRNA molecule is also referred to as being "directed to" or "targeted to" the gene to be silenced. The terms "silence," "inhibit the expression of," "down-regulate the expression of," "suppress the expression of" and the like in as far as they refer to a target gene, herein refer to the at least partial suppression of the expression of the target gene, as manifested by a reduction of the amount of mRNA which may be isolated from a first cell or group of cells in which the gene is transcribed and which has or have been contacted with the siRNA such that the expression of the gene is inhibited, as compared to a second cell or group of cells substantially identical to the first cell or group of cells but which has or have not been so contacted (control cells). Alternatively, the degree of inhibition may be given in terms of a reduction of a parameter that is a functionally linked expression of the gene, e.g., the amount of protein encoded by the target gene which is secreted by a cell, or the number of cells displaying a certain phenotype. Examples of genes where silencing may be desirable include oncogenes and genes where increased and/or aberrant expression of the gene is associated with a disease. As used herein, the term "oncogene" refers to a gene that has the potential to cause cancer. In cancerous cells, oncogenes are often mutated and/or expressed at high levels. An example of an oncogene is BCL2.

In one embodiment, the siRNA targets BCL2. BCL2 (B-cell Lymphoma) was originally characterized in a follicular lymphoma and is an anti-apoptotic cancer gene.

Various siRNAs containing azobenzene derivatives that target firefly luciferase are set out in Table 1.

Figure 3:
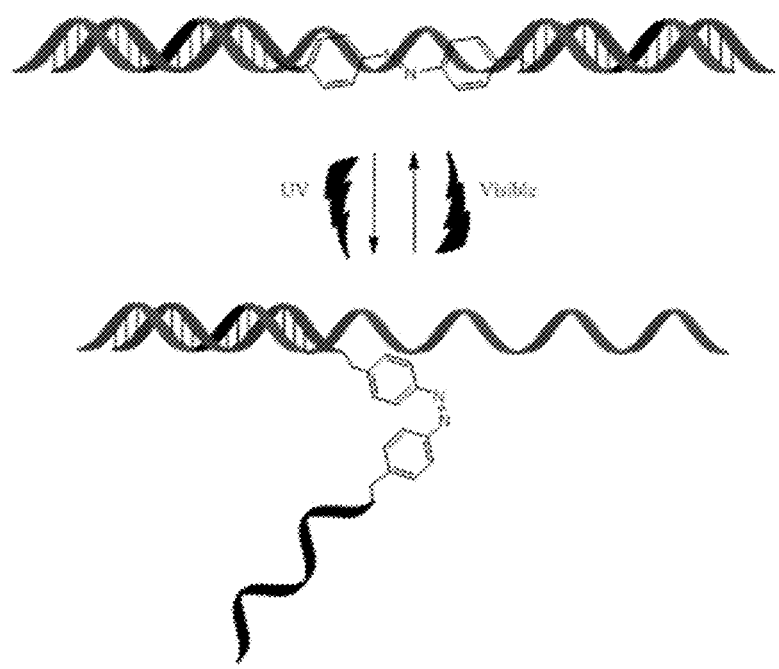
FIG. 3 shows photoinduced inactivation and reactivation of siRNAs.

As described above, azobenzene and derivatives thereof have photoswitchable properties. Specifically, the trans-isomer of azobenzene or an azobenzene derivative can be converted to the corresponding cis-isomer and vice versa upon exposure to particular wavelengths of light. The present inventors have shown that a chemically-modified siRNA comprising an azobenzene or derivative thereof in the trans form has gene silencing activity (i.e., the siRNA is functional), whereas the same chemically-modified siRNA comprising an azobenzene or derivative thereof in the trans form does not have gene silencing activity (i.e., the siRNA is non-functional). Without being bound by theory, it is believed that azobenzene, in the cis-form, distorts the siRNA, thus rendering it non-functional (see FIG. 3).

Accordingly, in one embodiment, the chemically-modified siRNA has RNA silencing activity when the azobenzene or derivative thereof is in the trans-configuration. In another embodiment, the chemically-modified siRNA does not have RNA silencing activity when the azobenzene or derivative thereof is in the cis-configuration. In another embodiment, the chemically-modified siRNA has higher RNA silencing activity when the azobenzene or derivative thereof is in the trans-configuration compared to the cis-configuration. Optionally, the chemically-modified siRNA has at least 10, 25, 50, 75, 100, 200 or 300% higher RNA silencing activity when the azobenzene or derivative thereof is in the trans-configuration compared to the cis-configuration.

Numerous methods for assaying RNA silencing activity are known in the art. In one embodiment, RNA silencing activity is indicated by reduced cellular mRNA or protein expression of the gene targeted by the siRNA. In one embodiment, reduced mRNA or protein expression of the gene targeted by the siRNA compared in cells containing the siRNA compared to cells not containing the siRNA indicates RNA silencing activity of the siRNA. mRNA or protein expression in cells containing the siRNA may be decreased by at least 5, 10, 25, 50, 75, 90 or 100% compared to cells not containing the siRNA.

In one embodiment, the azobenzene or derivative thereof contained in the siRNA undergoes isomerization from the trans-configuration to the cis-configuration in the presence of UV light. In another embodiment, the azobenzene or derivative thereof contained in the siRNA undergoes isomerization from the cis-configuration to the trans-configuration in the presence of visible light. In a further embodiment, the siRNA has higher RNA silencing activity when the azobenzene or derivative thereof is in the trans-configuration compared to the cis-configuration. Accordingly, the conversion of the azobenzene or derivative thereof contained in the siRNA from the trans-configuration to the cis-configuration is also referred to herein as "inactivating the siRNA" and the conversion of the azobenzene or derivative thereof contained in the siRNA from the cis-configuration to the trans-configuration is also referred to herein as "activating the siRNA". In other embodiments, the process of isomerization is reversible, such that the siRNA may be inactivated and inactivated more than one time.

In some embodiments, the wavelength for the trans-cis conversion is about 335 to 380 nm, 335 to 340 nm or about 365 nm and the wavelength for the cis-trans conversion is about 414 to 425 nm.

In further embodiments, the azobenzene or derivative thereof is a chlorinated azobenzene phosphoramidite. In such an embodiment, the chlorinated azobenzene phosphoramidite contained in the siRNA undergoes isomerization from the trans-configuration to the cis-configuration in the presence of green or red light and the chlorinated azobenzene phosphoramidite contained in the siRNA undergoes isomerization from the cis-configuration to the trans-configuration in the presence of blue and violet light. Accordingly, in another embodiment, the azobenzene or derivative thereof contained in the siRNA undergoes isomerization from the trans-configuration to the cis-configuration in the presence of green or red light and the azobenzene or derivative thereof contained in the siRNA undergoes isomerization from the cis-configuration to the trans-configuration in the presence of blue and violet light. In such embodiments, the wavelength for the trans-cis conversion is about 495 to 570 nm (green light) or 620 to 750 nm (red light) and the wavelength for the cis-trans conversion is about 450 to 495 nm (blue light) or 380 to 450 nm (violet light).

Light sources for providing visible light or UV light are well known in the art. In one embodiment, the light source for providing visible light is a regular daylight bulb, for example a 13 Watt (W) regular daylight bulb (available for example from NOMA). Other wattages, for example 5 to 20 W, optionally 10 W, 12 W, 13 W, 14 W, and 15 W, are also contemplated.

In another embodiment, the light source for providing UV light is a light source that provides UV light at about 365 nm, for example a hand held UV light. Various wattages, for example, 1 to 10 W, optionally 1 W, 2 W, 3 W, 4 W, 5 W, 6 W, 7 W, 8 W, 9 W or 10 W are contemplated.

Light sources for providing green, red, blue and/or violet light are also well known in the art. In one embodiment, the light source for providing green, red, blue and/or violet light is a light source that provides coloured light, for example a color LED light bulb such as an ilumi A19 Color LED Smart Light Bulb for the coloured light. In another embodiment, LED set ups for individual colours, and narrow bandwidth light filters are used. As will be appreciated by a person of skill in the art, different colors of light require different power inputs and outputs.

The duration of light exposure for both the trans to cis and the cis to trans conversion can be readily determined by a person of skill in the art. In one embodiment, 2 to 250 minutes, optionally about 5 to 120 minutes or 1 to 5 hours, optionally about 2, 3 or 4 hours of exposure to UV light, green light or red light is provided for the trans to cis conversion. In another embodiment, 2 to 250 minutes, optionally about 5 to 120 minutes or 1 to 5 hours, optionally about 2, 3 or 4 hours of exposure to visible light, blue light or violet light is provided for the cis to trans conversion. Much shorter durations of light exposure (for example, less than 10, 9, 8, 7, 6, 5, 4, 3, 2 or 1 minute) may also be used, as the inventors have shown that it is possible to cycle between cis and trans every five minutes.

Vector Encoded siRNAs

In another aspect, the siRNAs described herein are expressed from transcription units inserted into DNA or RNA vectors. These transgenes can be introduced as a linear construct, a circular plasmid, or a viral vector, which can be incorporated and inherited as a transgene integrated into the host genome. The transgene can also be constructed to permit it to be inherited as an extrachromosomal plasmid.

The sense and anti-sense strands of the siRNA can be transcribed by promoters on two separate expression vectors and co-transfected into a target cell. Alternatively each individual strand of the siRNA can be transcribed by promoters both of which are located on the same expression plasmid.

In one embodiment, a viral vector capable of accepting the coding sequences for the siRNA(s) to be expressed can be used, including, but not limited to, vectors derived from adenovirus (AV); adeno-associated virus (AAV); retroviruses (e.g., lentiviruses (LV), Rhabdoviruses, murine leukemia virus) and herpes.

Pharmaceutical Compositions

In another aspect, at least one embodiment of the present disclosure provides pharmaceutical compositions comprising a chemically-modified siRNA described herein as an active ingredient and a pharmaceutically acceptable carrier.

As used herein, the term "pharmaceutically acceptable carrier" is intended to include any and all solvents, dispersion media, coatings, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Optional examples of such carriers or diluents include, but are not limited to, water, saline, ringer's solutions, dextrose solution, and 5% human serum albumin.

A pharmaceutical composition is formulated to be compatible with its intended route of administration. Examples of routes of administration include parenteral, e.g. intravenous, intradermal, subcutaneous, oral (e.g. inhalation), transdermal (i.e., topical), transmucosal, and rectal administration.

In one embodiment, the active ingredient is prepared with a carrier that will protect it against rapid elimination from the body, such as a sustained/controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

In one embodiment, oral or parenteral compositions are formulated in dosage unit form for ease of administration and uniformity of dosage. Dosage unit form as used herein refers to physically discrete units suited as unitary dosages for the subject to be treated; each unit containing a predetermined quantity of active ingredient calculated to produce the desired therapeutic effect in association with the required pharmaceutical carrier. The specification for the dosage unit forms are dictated by and directly dependent on the unique characteristics of the active ingredient and the particular therapeutic effect to be achieved, and the limitations inherent in the art of preparing such an active ingredient for the treatment of individuals.

The formulation can also contain more than one active ingredient as necessary for the particular indication being treated, optionally those with complementary activities that do not adversely affect each other. Alternatively, or in addition, the pharmaceutical composition can comprise an agent that enhances its function. Such molecules are suitably present in combination in amounts that are effective for the purpose intended.

Methods and Uses
Methods of Activating and Inactivating an siRNA

In another aspect, at least one embodiment of the present disclosure is also directed to a method of activating and/or inactivating an siRNA molecule. The method comprises:

(a) providing a chemically-modified siRNA wherein one or more nucleotides of a strand of the siRNA are replaced with a spacer comprising an azobenzene or a derivative thereof, and (b) exposing the chemically-modified siRNA to light from a light source.

In one embodiment, the azobenzene or derivative thereof undergoes isomerization between the cis-configuration and the trans-configuration upon exposure to the light and wherein the chemically-modified siRNA has higher RNA silencing activity when the azobenzene or derivative thereof is in the trans-configuration compared to the cis-configuration.

In one embodiment, the light source provides UV light and the azobenzene or derivative thereof undergoes isomerization from the trans-configuration to the cis-configuration upon exposure to the UV light. In another embodiment, the light source provides visible light and the azobenzene or derivative thereof undergoes isomerization from the cis-configuration to the trans-configuration upon exposure to the visible light.

In one embodiment, the light source provides green and/or red light and the azobenzene or derivative thereof undergoes isomerization from the trans-configuration to the cis-configuration upon exposure to the green and/or red light. In another embodiment, the light source provides blue and/or violet light and the azobenzene or derivative thereof undergoes isomerization from the cis-configuration to the trans-configuration upon exposure to the blue and/or violet light.

In a further embodiment, the method comprises introducing the chemically-modified siRNA to a cell. The cell is optionally a bacterial cell, a fungal cell, a plant cell or a mammalian cell. In one embodiment, the cell is a human cell. The cell may be present in an organism or may be maintained in an in vitro cell culture. As used herein, the term "a cell" refers to both a single cell and a plurality of cells, for example two or more cells in culture.

"Introducing into a cell," as used herein when referring to siRNA, means facilitating uptake or absorption into the cell, as is understood by those skilled in the art. Various methods of introducing siRNA into a cell are known in the art. For example, siRNA may be delivered to a cell by way of transfection. Here, the siRNA is typically complexed with a carrier that allows it to transverse the cell membrane. In other embodiments, siRNA may be delivered to a cell via electroporation or through vector-based methods whereby DNA expression plasmids are used to express siRNA in cells. The meaning of this term is not limited to cells in vitro; siRNA may also be "introduced into a cell," wherein the cell is part of a living organism. In such instance, introduction into the cell will include the delivery to the organism. For example, for in vivo delivery, siRNA can be injected into a tissue site or administered systemically.

The siRNA may be exposed to light from a light source prior to being introduced into the cell. For example, the siRNA may be converted from its inactive to active form, or from its active to inactive form prior to transfection into the cell. Further, the siRNA may be exposed to light from a light source after its introduction into the cell. For example, the siRNA may be converted from its inactive to active form, or from its active to inactive form following transfection into the cell.

Multiple activations and inactivations of the chemically-modified siRNA are contemplated in the present disclosure. For example, the siRNA may be exposed to visible light such that azobenzene or derivative thereof undergoes isomerization from the cis-configuration to the trans-configuration, then exposed to UV light such that the azobenzene or derivative thereof undergoes isomerization from the trans-configuration back to the cis-configuration, then exposed again to visible light such that the azobenzene or derivative thereof undergoes isomerization again from the cis-configuration to the trans-configuration. Likewise, the siRNA may be exposed to UV light such that azobenzene or derivative thereof undergoes isomerization from the trans-configuration to the cis-configuration, then exposed to visible light such that the azobenzene or derivative thereof undergoes isomerization from the cis-configuration back to the trans-configuration, then exposed again to UV light such that the azobenzene or derivative thereof undergoes isomerization again from the cis-configuration to the trans-configuration.

In another example, the siRNA may be exposed to blue and/or violet light such that azobenzene or derivative thereof undergoes isomerization from the cis-configuration to the trans-configuration, then exposed to green and/or red light such that the azobenzene or derivative thereof undergoes isomerization from the trans-configuration back to the cis-configuration, then exposed again to blue and/or violet light such that the azobenzene or derivative thereof undergoes isomerization again from the cis-configuration to the trans-configuration. Likewise, the siRNA may be exposed to green and/or red light such that azobenzene or derivative thereof undergoes isomerization from the trans-configuration to the cis-configuration, then exposed to blue and/or violet light such that the azobenzene or derivative thereof undergoes isomerization from the cis-configuration back to the trans-configuration, then exposed again to green and/or red light such that the azobenzene or derivative thereof undergoes isomerization again from the cis-configuration to the trans-configuration.

Any of the above mentioned isomerizations may take place before the siRNA is introduced to a cell, after the siRNA is introduced to the cell, or a combination of the two.

In one embodiment, the chemically-modified siRNA is inactivated prior to cellular transfection to avoid exposing the cell to UV light.

Methods of Reversibly Silencing Gene Expression

In another aspect, in at least one embodiment, the present disclosure provides a method of reversibly silencing gene expression comprising:
(a) providing a chemically-modified siRNA wherein one or more nucleotides of a strand of the siRNA are replaced with a spacer comprising an azobenzene or a derivative thereof, and
(b) exposing the cell to light from a light source that modulates the cis-trans isomerism of the azobenzene or derivative thereof.

As used herein, the term "providing a cell with a chemically-modified siRNA" includes introducing the chemically-modified siRNA to a cell. The cell is optionally a bacterial cell, a plant cell or a mammalian cell. In one embodiment, the cell is a human cell. The cell may be present in an organism or may be maintained in an in vitro cell culture. As used herein, the term "a cell" refers to both a single cell and a plurality of cells, for example, two or more cells in culture.

As discussed above, various methods of introducing siRNA into a cell are known in the art including transfection, electroporation and vector-based methods whereby DNA expression plasmids are used to express siRNA in cells.

In one embodiment, expression of the gene is decreased compared to a control cell when the azobenzene or derivative thereof is in the trans-configuration. Levels of gene expression can be determined by using methods well known in the art. Reduction of gene expression is optionally compared to a control cell that has not been provided with the siRNA. In one embodiment, gene expression is decreased by at least 5, 10, 25, 75, 90, 95 or 100% compared to a control cell that has not been provided with the siRNA.

In another embodiment, expression of the gene is lower when the azobenzene or derivative thereof is in the trans-configuration compared to the cis-configuration. Optionally, the gene expression is at least 5, 10, 25, 50, 75, 90 or 100% lower when the azobenzene or derivative thereof is in the trans-configuration compared to the cis-configuration.

Methods of Treatment

In another aspect, in at least one embodiment, the chemically-modified siRNAs described herein may be useful for treating or preventing disease. In particular, the chemically-modified siRNAs may be useful for treating or preventing a disease associated with increased and/or aberrant expression of a gene, wherein the siRNA is directed to the gene. In addition, the chemically-modified siRNAs may be useful for treating or preventing a cancer, wherein the chemically-modified siRNA is directed to an oncogene. In one embodiment, the cancer is B-cell lymphoma and the siRNA is directed to BCL2.

In one embodiment, the chemically-modified siRNAs and pharmaceutical compositions described herein may be used in a method for treating or preventing a disease associated with increased and/or aberrant expression of a gene, the method comprising administering an effective amount of a chemically-modified siRNA or pharmaceutical composition disclosed herein to an animal or cell in need thereof, wherein the siRNA is directed to the gene.

In another embodiment, an effective amount of a chemically-modified siRNA or pharmaceutical composition disclosed herein may be used for treating or preventing a disease associated with increased and/or aberrant expression of a gene, wherein the siRNA is directed to the gene. In another embodiment, a chemically-modified siRNA or pharmaceutical composition disclosed herein may be used in the preparation of a medicament for treating or preventing a disease associated with increased and/or aberrant expression of a gene, wherein the siRNA is directed to the gene.

In one embodiment, the chemically-modified siRNAs and pharmaceutical compositions described herein may be used in a method for treating or preventing a cancer, the method comprising administering an effective amount of a chemically-modified siRNA or pharmaceutical composition disclosed herein to an animal or cell in need thereof, wherein the siRNA is directed to an oncogene.

In another embodiment, an effective amount of a chemically-modified siRNA or pharmaceutical composition disclosed herein may be used for treating or preventing a cancer, wherein the siRNA is directed to an oncogene. In another embodiment, a chemically-modified siRNA or pharmaceutical composition disclosed herein may be used in the preparation of a medicament for treating or preventing a cancer, wherein the siRNA is directed to an oncogene.

As used herein, the term "animal" includes all members of the animal kingdom. In one embodiment the animal is a mammal. In a further embodiment the animal is a human being. In one embodiment, the animal is a patient having a disease, such as a cancer.

An effective amount of a chemically-modified siRNA or pharmaceutical composition of the disclosure relates generally to the amount needed to achieve a therapeutic objective. Efficaciousness of treatment is determined in association with any known method for diagnosing or treating the particular disease. Alleviation of one or more symptoms of the disease indicates that the siRNA confers a clinical benefit.

As used herein, "treating or preventing" includes, but is not limited to, reversing, alleviating or inhibiting the progression of the disease or symptoms or conditions associated with the disease. Preventing includes preventing occurrence of the disease or symptoms or conditions associated with the disease or preventing worsening of the severity of the disease or symptoms or conditions associated with the disease. Accordingly, "treating or preventing the disease" optionally includes the prophylactic treatment of an animal or cell in order to prevent or reduce the incidence or recurrence of the cancer or symptoms or conditions associated with the disease.

In another embodiment, the chemically-modified siRNAs described herein are used as a tool for controlling the dose of a specific siRNA. For example, a certain amount of a chemically-modified siRNA may be injected into a cell or animal with a portion of it inactivated beforehand. Then, when a higher dose is required, the inactive portion is activated with visible light.

In another embodiment, the chemically-modified siRNAs described herein are used in gene therapy, in particular in cases where a temporal control would be beneficial. For example, if a gene starts to express aberrant mRNAs after a certain amount of time after exposure to a drug (for example, an antibiotic), the chemically-modified siRNAs described herein could be used to stop their expression into proteins which could interfere with the drug. In one embodiment, inactive chemically-modified siRNAs are co-injected with the drug, and then activated when necessary.

In yet another embodiment, thermal relaxation of the azobenzene back into its active trans form could also be utilized as a "set it and forget it" type of pharmaceutical where after injection the chemically-modified siRNA provides a kind of longer term knockdown of the target but at a lower dose. This strategy could be useful for applications where the drug is applied infrequently and an effective low dose is needed for a significant amount of time.

Methods of Research

Gene silencing is often desired in research applications. For example, gene silencing can be used to determine gene function, biological pathway function, study disease-related genes and identify new therapeutic targets. It would be advantageous to be able to selectively control temporally and/or spatially the activation of siRNAs, and therefore potentially any mRNA target, in research applications.

In one embodiment, the chemically-modified siRNAs described herein are used for targeting specific genes in a pathway. In particular, the siRNAs are used for selective turning on or off of genes at different time points, to see how that affects the pathway.

In another embodiment, the chemically-modified siRNAs described herein are used to disrupt cell signalling pathways. This allows the study of the effect the disruption of the pathway on any downstream processes in a time dependent manner. In one embodiment, cells are co-transfect with two siRNAs targeting different genes. One of the siRNAs is active and the other is inactive. After a certain amount of time, the second siRNA is also activated.

In one particular embodiment, the chemically-modified siRNAs described herein may be used to silence genes in a cell of a model organism. As used herein, the term "model organism" refers to a non-human species that has been studied to understand particular biological phenomena, with the expectation that discoveries made in the organism model will provide insight into the workings of other organisms. Examples of model organisms include, but are not limited to, *Escherichia coli, Saccharomyces cerevisiae, Schizosaccharomyces pombe, Drosophila melanogaster, Caenorhabditis elegans* and *Arabidopsis thaliana*.

The chemically-modified siRNAs described herein may also be used to create gene "knockdown" in animal models such as the mouse model *Mus musculus*. Methods of creating gene knockdowns using siRNA are well known in the art.

The following non-limiting Examples are illustrative of the present disclosure:

Example 1

One approach to controlling the activity of siRNAs involve using a light-dependent protection strategy, in which the nucleobase of an siRNA of interest is labeled with a photolabile group. In this state, the RNA is inactive, however, in the presence of light, the photolabile group is removed and proper hybridization ensues, and the RNA activity commences (Mikat et al, 2007). In 2005, Friedman synthesized a photocaged siRNA, and photoactivation and removal of the photocage led to active siRNAs (Shah et al, 2005). However, there are some issues with this approach. Removal of the photolabile group is irreversible, and the prolonged UV light exposure can harm the cells. As such, alternative approaches to the development of photoswitchable siRNAs are needed.

Azobenzene is an organic compound that has been around for decades (Beharry wt al, 2011). Despite its known photoswitchable properties, it has only relatively recently been used within oligonucleotides (Lubbe et al, 2017). For example, work by Asanuma and coworkers have designed photoswitchable DNA, in which an azobenzene monomer from recently, azobenzene C-nucleosides has been used to control DNA hybrid formation (Goldau et al, 2015). In a study by Tang and co-workers, they designed an azobenzene linked dumbbell, and via photoregulation, they were able to control the timing of RNA digestion of antisense oligonucleotides (Wu et al, 2015).

Recently, the synthesis and efficient RNAi knockdown of RNAs that contain a variety of functionalized spacer linkages within the central region of siRNAs was reported (Desaulniers et al, 2017; Efthymiou at al, 2012). Of notable importance, was the effect of utilizing a biphenyl (BP) aromatic spacer linkage within this position (Desaulniers et al, 2017). An siRNA bearing this modification within the central region of the sense strand of siRNAs exhibited potent downregulation effects.

Replacement of Two Nucleotides with Azobenzene within the Central Region of siRNAs Allows for Photochemical Control As shown in FIG. 1, two trans azobenzene phosphoramidites were synthesized, for their solid-phase incorporation within siRNAs. This involved taking either 4-nitrobenzyl alcohol or 4-nitrophenylethyl alcohol, and reducing the nitro group using basic conditions and zinc as an electron source to afford the diol compounds 1 and 4 in good yield. These diols reacted with 4'4-dimethoxytrityl (DMT) chloride to afford the monoalcohols 2 and 5. The DMT-protected diols were phosphitylated with 2-cyanoethyl diisopropylchlorophosphoramidite in the presence of trimethylamine to afford phosphoramidites 3 and 6.

Once the phosphoramidites were synthesized, a library of siRNAs containing azobenzene were generated that contain the modifications at the central region of the sense strand. Five different siRNA containing the azobenzene were synthesized that target the firefly luciferase mRNA (Table 1). In each case, the azobenzene derivative replaces two nucleotides on the oligonucleotide strand. These siRNAs were gel purified and characterized by mass spectrometry. SiRNA 7 contains an azobenzene modification (Az1; also referred to herein as Compound 3) that replaces positions 9 and 10, on the sense strand, counting from the 5'-end of the strand. This azobenzene insertion directly replaces the Argonaute 2 cleavage site. SiRNA 8 contains the Az1 azobenzene modification, Az1, at the 3'-end of the sense strand. SiRNAs 9-12 contain the other azobenzene modification (Az2; also referred to herein as Compound 6) and this modification spans two nucleotides that replace positions 8 and 9, 9 and 10, 10 and 11, and 11 and 12, of the sense strand, respectively. Finally, siRNA 13 contains the Az2 modification at the 3'-end of the sense strand.

Figure 2:
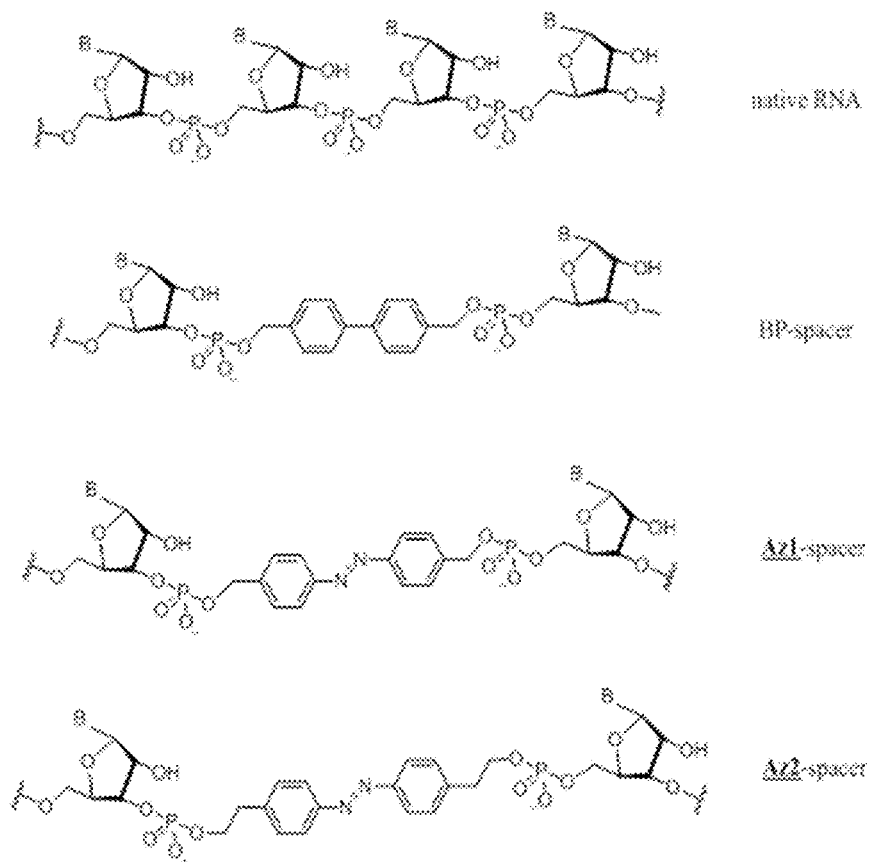
FIG. 2 shows structural differences between RNA, and RNAs containing a biphenyl group, and azobenzene groups. BP-spacer corresponds to a biphenyl functional group; Az1 and Az2 correspond to azobenzene derivatives.

FIG. 1 illustrates the structural differences between native RNA, a biphenyl-containing siRNA and azobenzene-containing siRNAs. FIG. 2 shows photoinduced inactivation and reactivation of azobenzene-containing siRNAs.

TABLE 1

Table of azobenzene-containing siRNAs[a]

| RNA | siRNA duplex | SEQ ID NO: |
|---|---|---|
| wt | 5'-CUUACGCUGAGUACUUCGAtt-3'<br>3'-ttGAAUGCGACUCAUGAAGCU-5' | 1<br>2 |
| 7 | 5'-CUUACGCUAz1GUACUUCGAtt-3'<br>3'-ttGAAUGCGACUCAUGAAGCU-5' | 3<br>4 |
| 8 | 5'-CUUACGCUGAGUACUUCGAAz1-3'<br>3'-ttGAAUGCGACUCAUGAAGCU-5' | 5<br>6 |
| 9 | 5'-CUUACGCAz2AGUACUUCGAtt-3'<br>3'-ttGAAUGCGACUCAUGAAGCU-5' | 7<br>8 |
| 10 | 5'-CUUACGCUAz2GUACUUCGAtt-3'<br>3'-ttGAAUGCGACUCAUGAAGCU-5' | 9<br>10 |
| 11 | 5'-CUUACGCUGAz2UACUUCGAtt-3'<br>3'-ttGAAUGCGACUCAUGAAGCU-5' | 11<br>12 |
| 12 | 5'-CUUACGCUGAAz2ACUUCGAtt-3'<br>3'-ttGAAUGCGACUCAUGAAGCU-5' | 13<br>14 |
| 13 | 5'-CUUACGCUGAGUACUUCGAAz2-3'<br>3'-ttGAAUGCGACUCAUGAAGCU-5' | 15<br>16 |

[a]Az1 corresponds to the azobenzene derivative synthesized from 4-nitrobenzyl alcohol; Az2 corresponds to the azobenzene derivative synthesized from 4-the nitrophenethyl alcohol; the top strand corresponds to the sense strand; bottom strand corresponds to the antisense strand. In all duplexes, the 5'-end of the bottom antisense strand contains a 5'-phosphate group.

Figure 4:
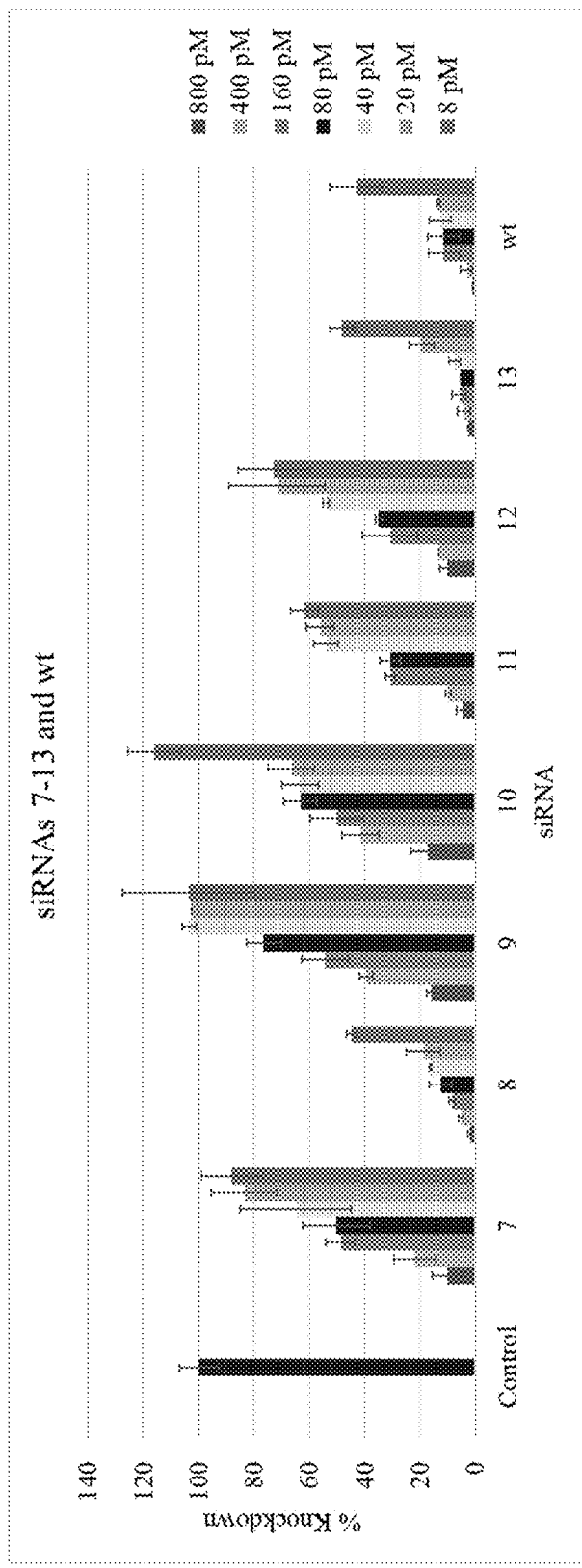
FIG. 4 shows a reduction in normalized firefly luciferase expression for siRNAs 7-13 and wt at 8, 20, 40, 80, 160, 400 and 800 pM concentrations in HeLa cells and lysed 22 h post transfection.

A dose-dependent assay was conducted to see if the siRNAs were functional in the native, trans form. As shown in FIG. 4, all the modified siRNAs exhibited dose-dependent gene silencing. Wild-type (Wt) siRNA and siRNAs 8 and 13 exhibited gene silencing at very similar levels. siRNAs 8 and 13 contain the azobenzene at the 3'-end of the sense strand. As such, there is no expectation that azobenzene would hinder the potency of the siRNA at this position, as several reports have indicated that aromatic bulky groups at the 3'-end of the sense strand are well accommodated by the RNA-induced silencing complex (RISC) (Ueno et al, 2009; Kitamura at al, 2013; Efthymiou et al, 2012). SiRNAs 9-12 exhibited lower potency gene silencing. This is not surprising as the azobenzene derivative does have quite a different structure from two nucleobases. However, they do function quite efficiently in the cell-based assay, and in a dose-dependent manner.

Figure 5:
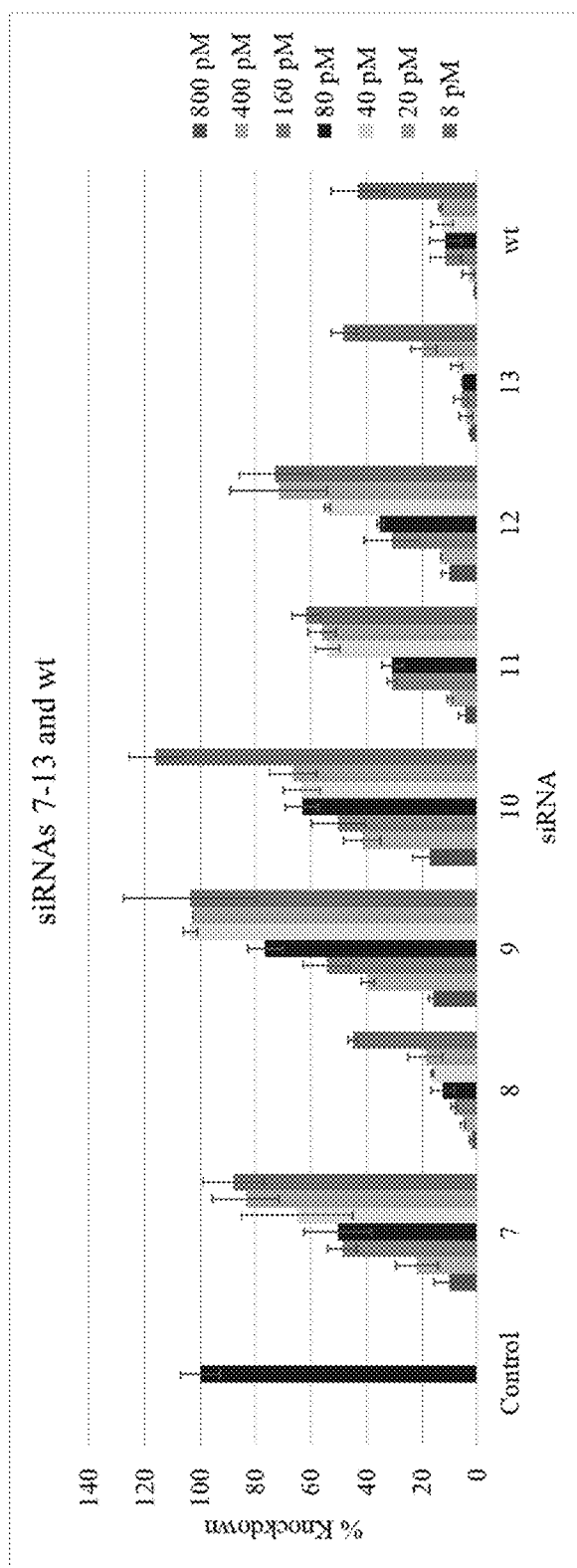
FIG. 5 shows a reduction in normalized firefly luciferase expression for siRNAs 7-13 and wildtype at a concentration of 800 pM in HeLa cells and lysed 16 h post transfection UV corresponds to the siRNA being exposed under a 365 nm UV lamp for inactivation prior to transfection. No light corresponds to siRNAs being transfected in HeLa cells in the absence of both UV and visible light.

Next, the siRNAs were screened to determine if they could be inactivated in the presence of UV light. Prior to transfection in HeLa cells, the siRNAs were incubated with UV light for two hours. 16 hours post transfection, the cells were lysed, and luciferase activity was measured. For siRNAs 7, 9, 10, 11, and 12, there was a clear reduction in activity with the siRNAs that were incubated with UV light, compared to ones that were not subjected to the UV light. As controls, the wild-type (wt) siRNA did not show any difference in activity, nor did siRNAs 8 and 13, which contain the azobenzene on the 3'-end as shown in FIG. 5.

Upon optimization, it was determined that 8 hours post-transfection was an ideal time frame to monitor changes in activity with siRNAs 7, and 9-12. In the following experiments, each siRNA was inactivated with UV light prior to transfection in order to characterize the inactivation effect of the azobenzene in its cis conformation. In FIG. 6A the inactivation effect of 800 pM of siRNA 7 can be clearly seen, which has a significant decrease in effectiveness at 8 hours compared to the no light treated sample.

Figure 6:
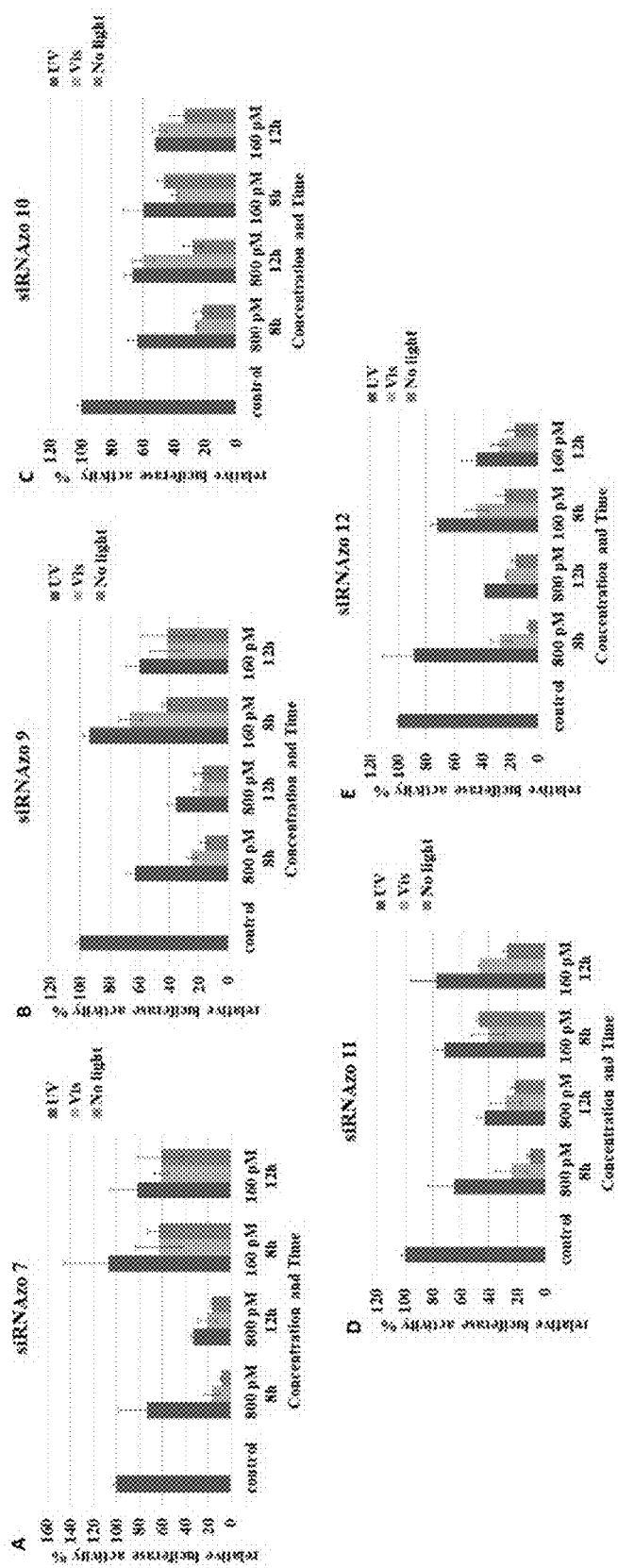
FIG. 6 shows a reduction in normalized firefly luciferase expression for siRNAs 7, 9, 10, 11, 12 (A, B, C, D, E respectively) at 160 and 800 pM in HeLa cells monitored 8 and 12 hours post-transfection. 1) UV corresponds to the siRNA being exposed under a 365 nm UV lamp for inactivation prior to transfection. 2) Vis corresponds to the siRNA being exposed under a 365 nm UV lamp for inactivation prior to transfection, however the transfected cells were exposed to a 13 W daylight lamp 4 hours post-transfection for the remainder of the transfection. 3) No light corresponds to siRNAs being transfected in HeLa cells in the absence of both UV and visible light.

It was also considered whether would be possible to reactivate the siRNA after in activation and transfection with visible light in order to resume siRNA activity. In order to test this, four hours after transfection the cells were exposed to the visible light for the remaining of the transfection. The siRNA resumed silencing activity, with only a small loss in activity as compared with the no light sample. This trend was observed for the 160 pM concentration as well, where inactivation reached control levels, and then activity was resumed with exposure to visible light, making it comparable with the no light sample in a similar manner. The 12 hour time points showed similar trends for both concentrations, but inactivation was less efficient. Without being bound by theory, it is believed that this loss in inefficiency is caused by the thermal relaxation of the azobenzene from cis to its more stable trans conformer, thus reactivating the siRNA over time, since it has been shown to have a half-life of about 4 hours at 37° C. In FIG. 6 (B through E), the same trend can be seen where the siRNAs with central region azobenzenes become inactivated under UV, reactivated with visible light, with the thermal relaxation phenomena at the 12 hour time points as well. Therefore, the siRNAs containing azobenzene at the central region of siRNAs exhibit photochemical control.

Figure 7:
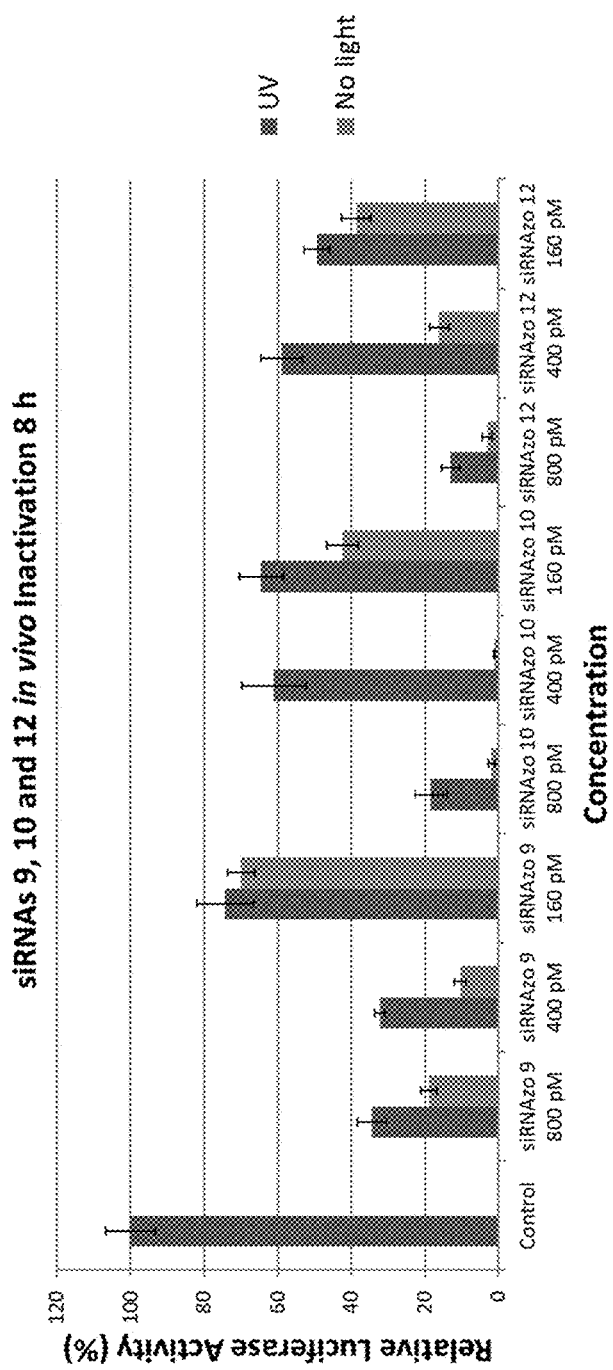
FIG. 7 shows a reduction in normalized firefly luciferase expression for siRNAs 9, 10, 12 at 160, 400 and 800 pM in HeLa cells monitored 8 hours post-transfection. 1) UV corresponds to the siRNA being exposed under a 365 nm UV lamp for inactivation 2 h post transfection for 45 min. 2) No light corresponds to siRNAs being transfected in HeLa cells in the absence of UV light.
Figure 8:
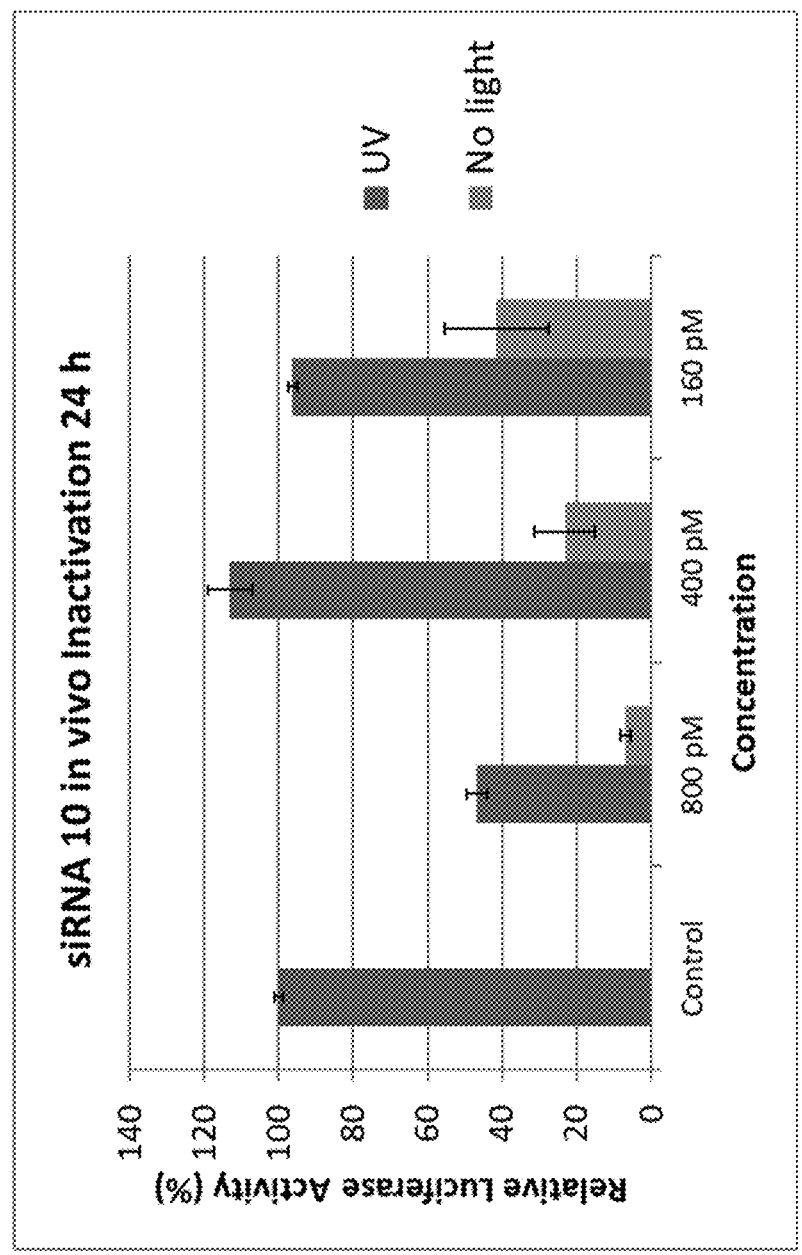
FIG. 8 shows a reduction in normalized firefly luciferase expression for siRNA 10 at 160, 400 and 800 pM in HeLa cells monitored 24 hours post-transfection. 1) UV corresponds to the siRNA being exposed under a 365 nm UV lamp for inactivation 2 h post transfection for 45 min, and for an additional 45 min of UV exposure every 4 hours (6 exposures total). 2) No light corresponds to siRNAs being transfected in HeLa cells in the absence of UV light.

In FIG. 7, light inactivation of azobenzene modified siRNA is seen 8 hours after transfection (trans to cis). In FIG. 8, light inactivation of azobenzene modified siRNA is seen 24 hours after transfection (trans to cis). It has therefore been demonstrated that azobenzene derivative spacers spanning the central region of an siRNA can be photochemically controlled. It has been shown that using UV light, the siRNAs can be inactivated in an efficient manner to almost control levels, and that reactivation can return the siRNA to untreated activity levels. This utilization of the azobenzenes natural photo-lability may allow the use of these siRNAs as therapeutics, such as cancer treatments or for use as a kind of gene therapy where an aberrant mRNA could be eliminated. To avoid off-target effects, an siRNA may be inactivated prior to administration via a delivery method, and activated to its site of interest via light. These modifications also allow better temporal and spatial control of siRNAs, and have applications in time sensitive dose control as well.

Methods

Unless otherwise indicated all starting reagents used were obtained from commercial sources without additional purification. Anhydrous $CH_2Cl_2$ and THF were purchased from Sigma-Aldrich and run through a PureSolv 400 solvent purification system to maintain purity. Flash column chromatography was performed with Silicycle Siliaflash 60 (230-400 mesh), using the procedure developed by Still, Kahn and Mitra[1]. NMRs were performed on a Varian 400 MHz spectrophotometer. All $^1H$ NMRs were recorded for 64 transients at 400 MHz and all $^{13}C$ NMRs were run for 1500 transients at 101 MHz and all $^{31}P$ NMRs were recorded for 256 transients at 167 MHz. Spectra were processed and integrated using ACD labs NMR Processor Academic Edition.

Synthesis of Compound 1.
4,4'-bis(hydroxyethyl)-azobenzene 4 g of 4-nitrophenethyl alcohol and 6 g of Zn powder was added to 90 mL of 5.7M NaOH(aq) solution. After refluxing overnight (10-16 h) to facilitate the reaction, it was then filtered on a Buchner Vacuum filter, suspending the crystals in hot methanol. The crystals were collected and filtered again with a gravity filter to remove residual salts and then the methanol solution was removed using a rotary evaporator, crystals collected and purified on silica gel column using 5% MeOH/95% DCM. This afforded 2.34 g of orange crystals in a 70% yield. $^1$H NMR (400 MHz, DMSO) δ 7.75-7.81 (d, 4H) 7.41 (d, 4H) 4.71 (t, 2H) 3.65 (td, 4H) 2.80 (t, 4H). $^{13}$C NMR (101 MHz, DMSO) 150.84, 144.02, 130.34, 122.79, 62.26, 38.87; ESI-HRMS (ES$^+$) m/z calculated for $C_{16}H_{18}N_2O_2$: 271.1441, found 271.1438 [M+H]$^+$.

Synthesis of Compound 2. 4-hydroxyethyl-4'-O-(4,4'dimethoxytrityl)-azobenzene 1.5 g of Compound 1 was dissolved in 30 mL of anhydrous THF and 1.95 g (1 eq) of 4,4'-dimethoxytrityl chloride was added along with 2.5 mL (3 eq) of trimethylamine. The reaction mixture was stirred vigorously overnight (10-16 h), monitored by TLC. It was then concentrated on rotovap and purified on silica gel 5% MeOH/95% DCM to afford orange crystals, 35% yield. $^1$H NMR (400 MHz, CDCl$_3$) δ 7.87 (td, 6H) 7.45-7.47 (m, 2H) 7.24-7.40 (m, 3H) 7.18-7.22 (m, 5H) 6.80-6.87 (m, 4H) 3.91 (t, 2H) 3.75-3.82 (s, 6H) 3.36 (t, 2H) 3.07 (s, 1H) 2.94-2.98 (m, 4H). $^{13}$C NMR (101 MHz, CDCl$_3$) δ 158.37, 151.50, 151.45, 151.31, 151.27, 145.13, 143.11 142.97, 142.00, 141.87, 136.39, 130.02, 130.00, 129.95, 129.93, 129.75, 129.73, 129.32 129.28, 129.17, 128.16, 127.85, 127.80, 127.76, 127.70, 126.65, 123.02, 122.99, 122.75 122.71, 120.94, 120.51, 113.17 113.05, 113.00, 86.07, 77.42, 77.10, 76.78, 67.97, 64.40 63.42, 63.39, 55.25, 55.20, 53.46; ESI-HRMS (ES$^+$) m/z calculated for $C_{37}H_{36}N_2O_4$: 573.2748, found 573.2741 [M+H]$^+$.

Synthesis of Compound 3. 2-Cyanoethyl-4-O-{[4-hydroxyethyl-4'-O-(4,4'dimethoxytrityl)-O-methyl-diazenyl]}-N,N'-diisopropylaminophosphoramidite 0.26 g of Compound 2 was taken and dissolved in 4 mL of anhydrous DCM/ACN (1:1) in a flame dried flask. To that solution 0.63 mL (10 eq) of anhydrous triethylamine was added along with 0.3 mL (3 eq) of 2-Cyanoethyl N,N-diisopropylchlorophosphoramidite and allowed to stir until TLC showed starting materials were consumed (about 3 hours). The compound was then purified on silica gel using a 68%:30%:2% hexanes/ethyl acetate/triethylamine mobile phase. This afforded an orange oil of 0.22 g, 63% yield. $^1$H NMR (400 MHz, CDCl$_3$) δ 7.82-7.88 (m, 4H) 7.32-7.41 (m, 6H) 7.27-7.30 (m, 4H) 7.21-7.25 (m, 3H) 6.84 (d, 4H) 6.76-6.81 (m, 3H) 4.13 (q, 2H) 3.84-3.94 (m, 1H) 3.75-3.81 (m, 6H) 3.55-3.67 (m, 1H) 3.35 (t, 2H) 2.93-2.98 (t, 2H) 1.50 (d, 1H) 1.27 (t, 6H) 1.17 (dd, 6H). $^{13}$C NMR (101 MHz, CDCl$_3$) δ 158.62, 158.35, 151.29, 145.10, 142.93, 136.35, 130.07, 129.99, 129.90, 129.75, 129.13, 128.13, 127.83, 127.77, 127.72, 127.04, 126.61, 122.78, 122.70, 122.67, 113.15 113.01 112.96 86.04 77.37 77.06 76.74 64.38 60.37 55.23 55.18 43.14 43.02 36.66, 24.67, 24.59 24.51 21.04 14.20. ESI-HRMS (ES$^+$) m/z calculated for $C_{46}H_{53}N_4O_5P$: 772.4797, found 703.3949 [M+H]$^+$ (Hydrolyzed product).

Synthesis of Compound 4. 4,4'-bis(hydroxymethyl)-azobenzene 4 g of 4-nitrophenethyl alcohol and 6 g of Zn powder was added to 90 mL of 5.7M NaOH(aq) solution. After refluxing overnight (10-16 h) to facilitate the reaction, it was then filtered on a Buchner Vacuum filter, suspending the crystals in hot methanol. The crystals were collected and filtered again with a gravity filter to remove residual salts and then the methanol solution was removed using a rotary evaporator, crystals collected and purified on silica gel column using 5% MeOH/95% DCM. This afforded 2.34 g of orange crystals in a 70% yield. $^1$H NMR (400 MHz, DMSO) δ 7.85 (d, 4H) 7.51 (d, 4H) 5.35 (s, 2H) 4.59 (d, 4H). $^{13}$C NMR (101 MHz, DMSO) δ 105.84, 146.24, 127.09, 122.34, 63.43. ESI-HRMS (ES$^+$) m/z calculated for $C_{14}H_{14}N_2O_2$: 243.1128, found 243.1126 [M+H]$^+$.

Synthesis of Compound 5. 4-hydroxymethyl-4'-O-(4,4'dimethoxytrityl)-azobenzene 1.5 g of Compound 1 was dissolved in 30 mL of anhydrous THF and 1.95 g (1 eq) of 4,4'-dimethoxytrityl chloride was added along with 2.5 mL (3 eq) of trimethylamine. The reaction mixture was stirred vigorously overnight (10-16 h), monitored by TLC. It was then concentrated on rotovap and purified on silica gel 5% MeOH/95% DCM to afford orange crystals, 35% yield. $^1$H NMR (400 MHz, DMSO): δ 7.87 (m, 4H) 7.51 (m, 6H) 7.44 (m, 4H) 7.32 (m, 3H) 6.82 (m, 4H) 4.59 (s, 2H) 4.18 (s, 2H) 3.72 (m, 6H). $^{13}$C NMR (101 MHz, DMSO) δ 158.63, 158.25, 151.31, 146.69, 145.29, 140.68, 135.99, 130.11, 129.36, 128.43, 128.09, 127.93, 127.84, 127.56, 123.03, 122.80, 113.79, 113.20, 86.56, 62.90, 55.50, 55.44; ESI-HRMS (ES$^+$) m/z calculated for $C_{35}H_{32}N_2O_4$: 545.2435, found 545.2430 [M+H]$^+$.

Synthesis of Compound 6. 2-Cyanoethyl-4-O-{[4-hydroxymethyl-4'-O-(4,4'dimethoxytrityl)-O-methyl-diazenyl]}-N,N'-diisopropylaminophosphoramidite 0.247 g of Compound 2 was taken and dissolved in 4 mL of anhydrous DCM/ACN (1:1) in a flame dried flask. To that solution 0.63 mL (10 eq) of anhydrous trimethylamine was added along with 0.3 mL (3 eq) of 2-Cyanoethyl N,N-diisopropylchlorophosphoramidite and allowed to stir until TLC showed starting materials were consumed (about 3 hours). The compound was then purified on silica gel using a 68%:30%:2% hexanes/ethyl acetate/triethylamine mobile phase. This afforded an orange oil of 0.12 g, 33% yield. $^1$H NMR (400 MHz, CDCl$_3$) δ 7.88-7.94 (m, 4H) 7.50-7.56 (m, 5H) 7.39-7.45 (m, 3H) 7.29-7.33 (m, 1H) 6.83-6.89 (m, 4H) 4.80 (dd, 1H) 4.26 (s, 2H) 4.09-4.16 (m, 1H) 3.82-3.93 (m, 2H) 3.79-3.81 (m, 6H) 3.59-3.73 (m, 2H) 2.62-2.68 (m, 2H) 1.18-1.25 (m, 12H).

Maintaining Cell Cultures

For biological analysis of these siRNAs in a live environment, human epithelial cervix carcinoma cells were used (HeLa cells). They were kept in 250 mL vented culture flasks using 25 mL of DMEM with 10% fetal bovine serum and 1% penicillin-streptomycin (Sigma) in an incubator set for 37° C. @ 5% $CO_2$ humidified atmosphere.

Once cell lines became confluent (80-90%) they were passaged by washing 3 times with 10 mL of phosphate buffered saline (NaCl 137 mM, KCl 2.7 mM, $PO_4^{3-}$ 10 mM, pH 7.4) and incubated with 3 mL of 0.25% trypsin (SAFC bioscience) for 4 min @ 37° C. to detach the cells. The cells were transferred to a 50 mL centrifuge tube after the addition of 10 mL of DMEM solution and pelleted at 2000 rpm for 5 minutes. The supernatant was discarded and the pellet resuspended in 5 mL DMEM with 10% FBS.

A standard haemocytometer was used to obtain cell counts, after which the cells were diluted to a final concentration of 1×10$^6$ cells/mL for subsequent assays. To continue the cell line 1 mL of freshly passaged cells was added to 24 mL of DMEM/10% FBS and 1% penicillin-streptomycin at 37° C. in a new culture flask while the rest were used for assays.

Procedure for siRNA Transfection 100 ul of cells (total 1×10$^5$) were transfected into 12 well plates (Falcon®) with 1 mL of DMEM (10% FBS, 1% penicillin-streptomycin) and incubated at 37° C. with 5% $CO_2$. After 24 hours the cells were transfected with various concentrations of siRNAs, along with both pGL3 (Promega) and pRLSV40 luciferase plasmids using Lipofectamine 2000 (Invitrogen) in Gibco's 1× Opti-Mem reduced serum media (Invitrogen) according to the manufacturer's instructions. 1 uL of siRNA was added along with 2 uL (pGL3 200 ng) and 0.5 uL pRLSV40 (50 ng) to 100 uL of 1× Opti-Mem in a microcentrifuge tube and kept on ice for 5 min. In a different microcentrifuge tube 1 uL of Lipofectamine 2000 (Invitrogen) was mixed with 100 uL of Gibco's 1× Opti-Mem reduced serum media (Invitrogen) and incubated at room temperature for 5 min. After 5 minutes the tubes were mixed and incubated at room temperature for 20 min and then the entire contents transferred to the wells of the 12 well plate.

Procedure for Light Inactivation of Azobenzene Modified siRNA (Trans to Cis)

1 uL of the desired siRNA was added to a microcentrifuge tube and exposed to a 4 W 365 nm UV lamp (UVP) and was exposed for at least 4 hours. Longer exposure times required the addition of a small amount of RNAse free water to prevent evaporation.

After UV exposure the siRNA can be used in the transfection procedure above, but the transfection must be done in the dark room, to prevent the cis to trans conversion back into the active form.

Procedure for Light Reactivation of Azobenzene Modified siRNA (Cis to Trans)

4 hours after the transfection procedure, the plate was exposed to a 13 W daylight bulb (NOMA) and left under the visible lamp for the rest of the time before the cells were lysed and the plate read as above.

Procedure for Light Inactivation of Azobenzene Modified siRNA After Transfection 8 h (Trans to Cis)

The transfected 12 well plate was exposed to a 4.00 W 365 nm UV lamp (UVP) and was exposed for 45 min 2 h post transfection. After UV exposure the desired wells on the plate were lysed at the 8 h time point and the dual luciferase kit was used to determine relative luciferase activity.

Procedure for Light Inactivation of Azobenzene Modified siRNA After Transfection 24 h (Trans to Cis)

The transfected 12 well plate was exposed to a 4.00 W 365 nm UV lamp (UVP) and was exposed for 45 min 2 h post transfection. Every 4 h thereafter the plate was exposed to a 45 min period of UV light, 6 exposures total. After UV exposure the desired wells on the plate were lysed at the 24 h time point and the dual luciferase kit was used to determine relative luciferase activity.

Example 2. Synthesis of Chlorinated Azobenzene Phosphoramidites

Figure 9:
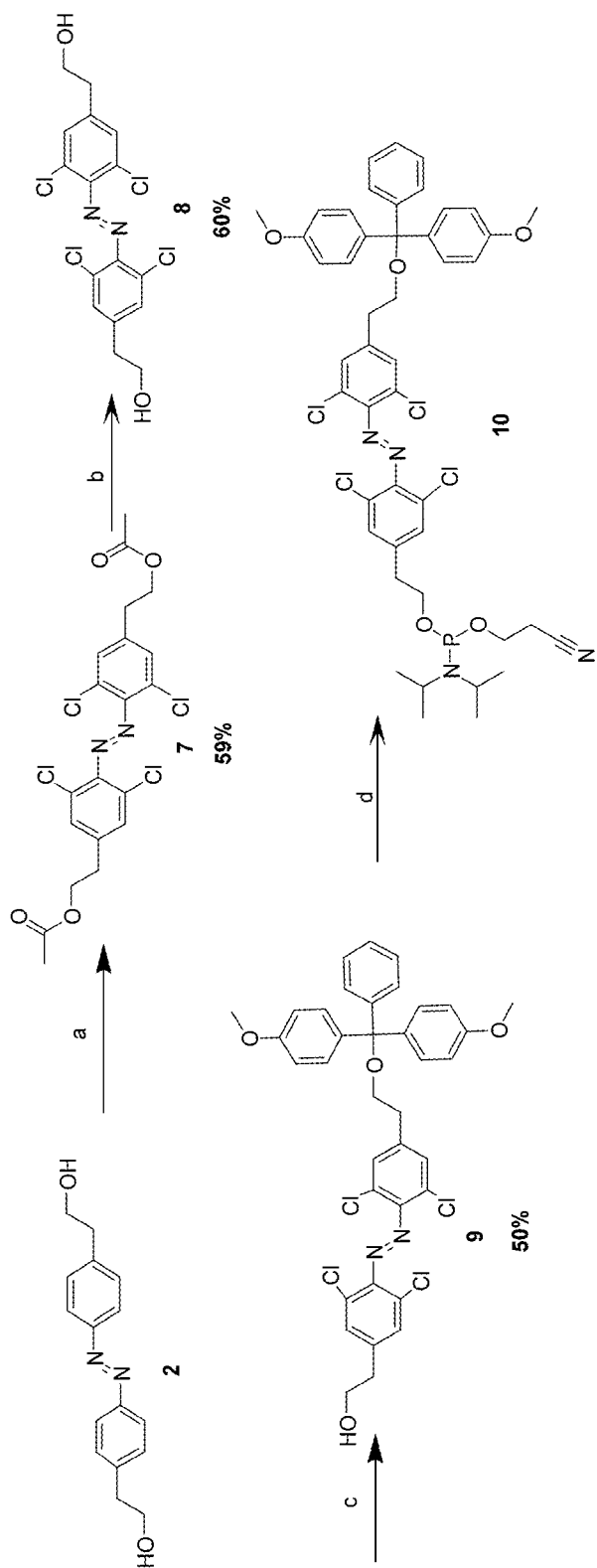
FIG. 9 shows the synthesis of chlorinated azobenzene phosphoramidites: (a) 0.3 equiv. of $Pd(OAc)_2$ and 8 equiv. of NCS, AcOH, reflux overnight @ 145° C., 59% (7); (b) 0.1 eq NaOH in MeOH, r.t. 0.5 h, 60% (8); (c) 1 equiv. dimethoxytrityl chloride (DMT-Cl), 3 equiv. TEA, THF, r.t., 50% (9); (c) 3 equiv. of 2-cyanoethyl N,N-diisopropylchlorophosphoramidite, 10 equiv. TEA, anh. DCM:ACN (1:1), r.t. 1.5 h, 60% (10).

Chlorinated azobenzene phosphoramidites were synthesized using the following method (see also FIG. 9):

Synthesis of Compound 7. (E)-(diazene-1,2-diylbis (3,5-dichloro-4,1-phenylene))bis(ethane-2,1-diyl) diacetate 0.2 g of Compound 2 was dissolved in 4 mL of AcOH and 0.04 g (0.3 eq) of Pd(OAc)$_2$ was added along with 1.95 g (8 eq) of NCS. The reaction mixture was stirred vigorously overnight (24 h) @ 145° C., monitored by TLC. It was then concentrated on rotovap and purified on silica gel 2% Acetone/98% ether to afford red crystals, 59% yield.

Synthesis of Compound 8. (E)-2,2'-(diazene-1,2-diylbis(3,5-dichloro-4,1-phenylene))bis(ethan-1-ol)

0.2 g of Compound 7 was dissolved in 4 mL of MeOH and 0.2 g (0.2 eq) of NaOH. The reaction mixture was stirred vigorously for 2 h @ r.t., monitored by TLC. It was then concentrated on rotovap and purified on silica gel 5% MeOH/95% DCM to afford red crystals, 60% yield.

Synthesis of Compound 9. (E)-2-(4-((4-(2-(bis(4-methoxyphenyl)(phenyl)methoxy)ethyl)-2,6-dichlorophenyl)diazenyl)-3,5-dichlorophenyl)ethan-1-ol 0.2 g of Compound 8 was dissolved in 10 mL of anhydrous THF and 0.3 g (1 eq) of 4,4'-dimethoxytrityl chloride was added along with 0.2 mL (3 eq) of trimethylamine. The reaction mixture was stirred vigorously overnight (10-16 h), monitored by TLC. It was then concentrated on rotovap and purified on silica gel 5% MeOH/95% DCM to afford orange crystals, 50% yield.

Synthesis of Compound 10. (E)-4-((4-(2-(bis(4-methoxyphenyl)(phenyl)methoxy)ethyl)-2,6-dichlorophenyl)diazenyl)-3,5-dichlorophenethyl (2-cyanoethyl) diisopropylphosphoramidite 0.15 g of Compound 9 was taken and dissolved in 4 mL of anhydrous DCM/ACN (1:1) in a flame dried flask. To that solution 0.3 mL (10 eq) of anhydrous trimethylamine was added along with 0.131 mL (3 eq) of 2-Cyanoethyl N,N-diisopropylchlorophosphoramidite and allowed to stir until TLC showed starting materials were consumed (about 2 hours). The compound was then purified on silica gel using a 68%:30%:2% hexanes/ethyl acetate/triethylamine mobile phase. This afforded a red oil of 0.10 g, 60% yield.

Figure 10:
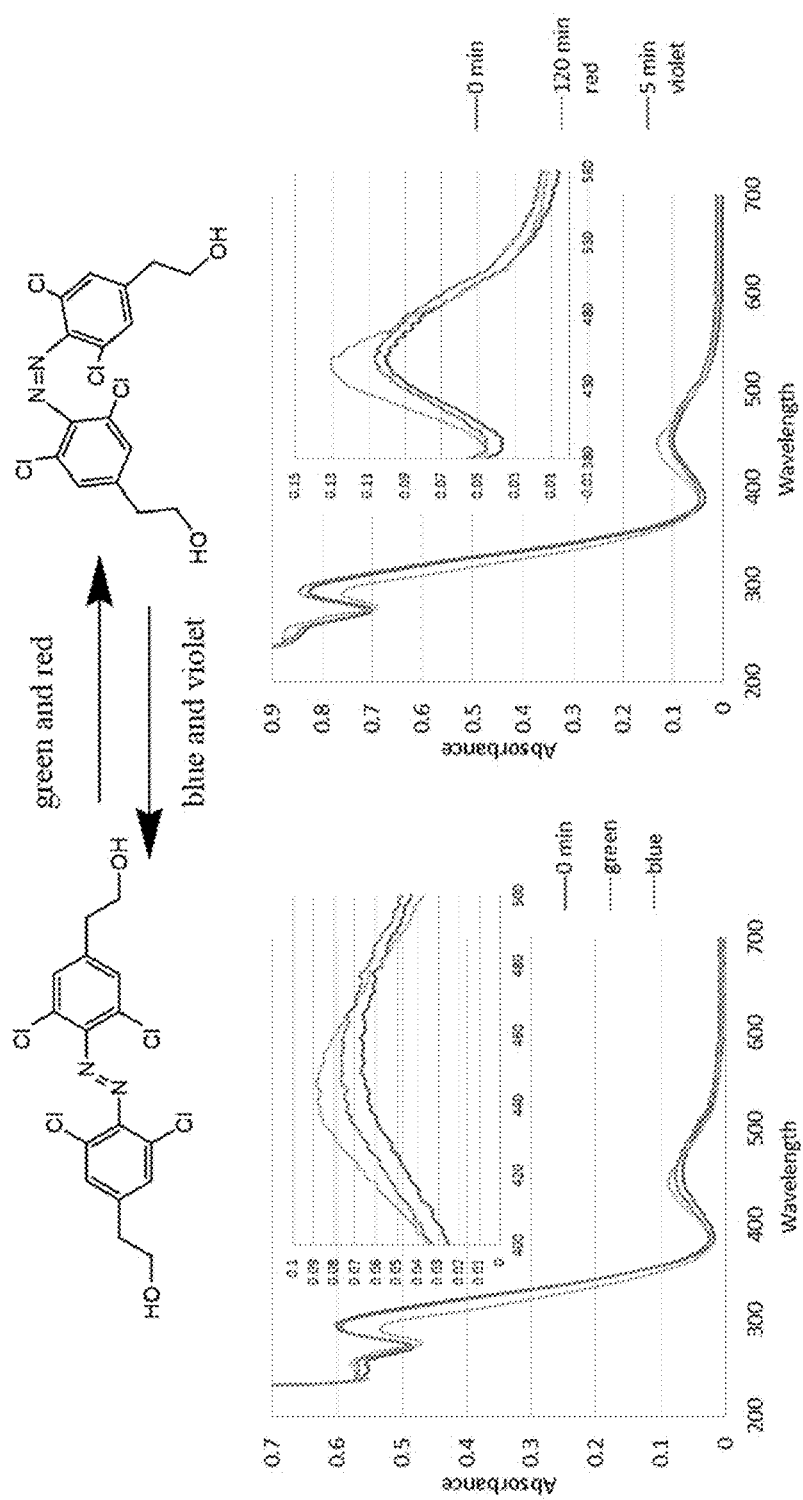
FIG. 10 shows the absorbance profile of compound 8 when exposed to various wavelengths of visible light in 500 µL of HPLC grade MeOH and scanned from 200-700 nm at 10° C. with a screening rate of 20.0 nm/min and a 0.20 nm data pitch. Inset: Zoomed in portion of 380-580 nm highlighting compound 8 changes.

As shown in FIG. 10, the ortho-position chlorines affect the absorbance profile of the azobenzene derivative. The left shows maximum absorbance when exposed to 15 min of green light (495-570 nm), then 15 min of blue light (450-495 nm). There is a clear change in the maximum absorbance during the isomerization from trans to cis (green) and then it is restored back to trans when exposed to blue light. The right graph shows the same, except with 120 minute exposure to red light (620-750 nm) to isomerize to cis, and 5 min violet light (380-450 nm) to change it back to trans.

Figure 11:
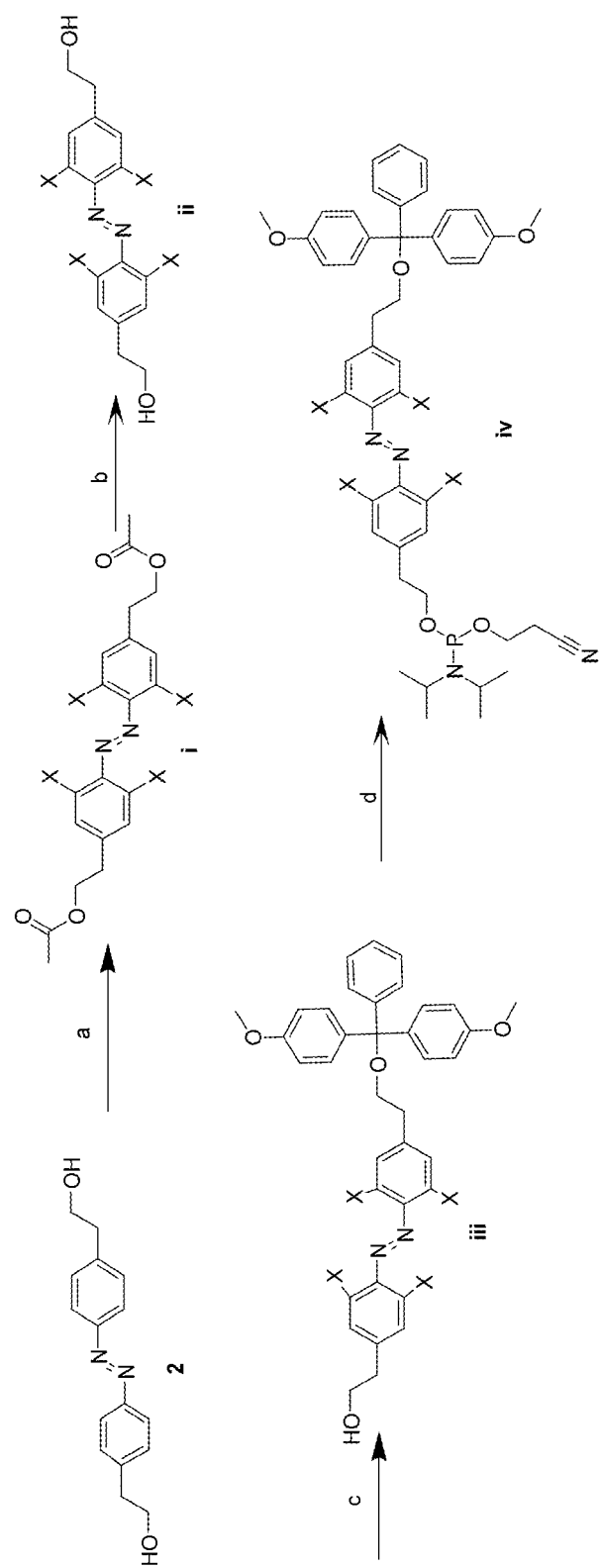
FIG. 11 shows a general reaction scheme similar to FIG. 9, where X=Br, F, I, —OMe, —OEt, —$NH_2$, —$SO_2$, —$NO_2$ groups in the ortho position on the phenyl rings.

Other groups in the ortho position on the phenyl rings (for example where X=Br, F, I, —OMe, —OEt, —$NH_2$, —$SO_2$, —$NO_2$) are also contemplated as shown in FIG. 11.

REFERENCES

Braasch, D. A.; Jensen, S.; Liu, Y.; Kaur, K.; Arar, K.; White, M. A.; Corey, D. R., RNA interference in mammalian cells by chemically-modified RNA. Biochemistry 2003, 42 (26), 7967-75.

Selvam, C.; Mutisya, D.; Prakash, S.; Ranganna, K.; Thilagavathi, R., Therapeutic potential of chemically modified siRNA: Recent trends. Chem Biol Drug Des 2017.

Lee, S. H.; Kang, Y. Y.; Jang, H. E.; Mok, H., Current preclinical small interfering RNA (siRNA)-based conjugate systems for RNA therapeutics. Adv Drug Deliv Rev 2016, 104, 78-92.

Corey, D. R., Chemical modification: the key to clinical application of RNA interference? Journal of Clinical Investigation 2007, 117 (12), 3615-3622.

Kitamura, Y., Synthesis of Nucleic Acid Mimics and Their Application in Nucleic Acid-based Medicine. Yakugaku zasshi: Journal of the Pharmaceutical Society of Japan 2016, 136 (11), 1491-1499.

Young, S. W.; Stenzel, M.; Yang, J. L., Nanoparticle-siRNA: A potential cancer therapy? Critical reviews in oncology/hematology 2016, 98, 159-69.

Mikat, V.; Heckel, A., Light-dependent RNA interference with nucleobase-caged siRNAs. RNA (New York, N.Y.) 2007, 13 (12), 2341-7.

Shah, S.; Rangarajan, S.; Friedman, S. H., Light-activated RNA interference. Angewandte Chemie (International ed. in English) 2005, 44 (9), 1328-32.

Beharry, A. A.; Woolley, G. A., Azobenzene photoswitches for biomolecules. Chem Soc Rev 2011, 40 (8), 4422-37.

Lubbe, A. S.; Szymanski, W.; Feringa, B. L., Recent developments in reversible photoregulation of oligonucleotide structure and function. Chem Soc Rev 2017, 46 (4), 1052-1079.

Kashida, H.; Fujii, T.; Asanuma, H., Threoninol as a scaffold of dyes (threoninol-nucleotide) and their stable interstrand clustering in duplexes. Org Biomol Chem 2008, 6 (16), 2892-9.

Goldau, T.; Murayama, K.; Brieke, C.; Asanuma, H.; Heckel, A., Azobenzene C-Nucleosides for Photocontrolled Hybridization of DNA at Room Temperature. Chemistry (Weinheim an der Bergstrasse, Germany) 2015, 21 (49), 17870-6.

Wu, L.; He, Y.; Tang, X., Photoregulating RNA digestion using azobenzene linked dumbbell antisense oligodeoxynucleotides. Bioconjug Chem 2015, 26 (6), 1070-9.

Desaulniers, J.-P.; Hagen, G.; Anderson, J.; McKim, C.; Roberts, B., Effective gene-silencing of siRNAs that contain functionalized spacer linkages within the central region. RSC Advances 2017, 7 (6), 3450-3454.

Efthymiou, T. C.; Peel, B.; Huynh, V.; Desaulniers, J. P., Evaluation of siRNAs that contain internal variable-length spacer linkages. Bioorganic & Medicinal Chemistry Letters 2012, 22 (17), 5590-5594.

Ueno, Y.; Watanabe, Y.; Shibata, A.; Yoshikawa, K.; Takano, T.; Kohara, M.; Kitade, Y., Synthesis of nuclease-resistant siRNAs possessing universal overhangs. Bioorg Med Chem 2009, 17 (5), 1974-81.

Kitamura, Y.; Masegi, Y.; Ogawa, S.; Nakashima, R.; Akao, Y.; Ueno, Y.; Kitade, Y., Chemically modified siRNAs and miRNAs bearing urea/thiourea-bridged aromatic compounds at their 3'-end for RNAi therapy. Bioorg Med Chem 2013, 21 (15), 4494-501.

Efthymiou, T. C.; Vanthi, H.; Oentoro, J.; Peel, B.; Desaulniers, J.-P., Efficient synthesis and cell-based silencing activity of siRNAS that contain triazole backbone linkages. Bioorganic & Medicinal Chemistry Letters 2012, 22 (4), 1722-1726.

Beharry, A. A.; Woolley, G. A., Azobenzene photoswitches for biomolecules. *Chemical Society Reviews* 2011, 40, 4422-4437.

Collingwood, M. A.; Rose, S. D.; Huang, L. Y.; Hillier, C.; Amarzguioui, M.; Wiiger, M. T.; Soifer, H. S.; Rossi, J. J.; Behlke, M. A., Chemical modification patterns compatible with high potency Dicer-substrate small interfering RNAs. *Oligonucleotides* 2008, 18, 187-199.

Wu, L.; He, Y. J.; Tang, X. J., Photoregulating RNA Digestion Using Azobenzene Linked Dumbbell Antisense Oligodeoxynucleotides. *Bioconjugate Chemistry* 2015, 26, 1070-1079.

Lubbe, A. S.; Szymanski, W.; Feringa, B. L., Recent developments in reversible photoregulation of oligonucleotide structure and function. *Chemical Society Reviews* 2017, 46, 1052-1079.

The invention claimed is:

1. A chemically-modified siRNA wherein one or more nucleotides of a strand of the siRNA are replaced with a spacer comprising an azobenzene or a derivative thereof.

2. The siRNA of claim 1, wherein the one or more nucleotides the spacer replaces are located in the sense strand of the siRNA.

3. The siRNA of claim 1, wherein two nucleotides of the strand are replaced by the spacer comprising the azobenzene or derivative thereof.

4. The siRNA of claim 1, wherein the spacer comprising the azobenzene or the derivative thereof is a compound of Formula I:

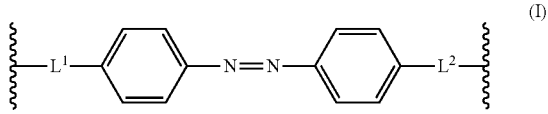

(I)

wherein
$L^1$ and $L^2$ are each independently a linker moiety; and
one or more available hydrogen atoms on the phenyl rings is optionally replaced with another group, and optionally, wherein $L^1$ and $L^2$ are each independently $C_{1-6}$alkylene, optionally wherein $L^1$ and $L^2$ are each methylene or ethylene.

5. The siRNA of claim 1, wherein the azobenzene or derivative thereof undergoes isomerization from the trans-configuration to the cis-configuration in the presence of UV light and/or undergoes isomerization from the cis-configuration to the trans-configuration in the presence of visible light.

6. The siRNA of claim 5, wherein the isomerization from the trans-configuration to the cis-configuration is reversible in the presence of visible light and/or the isomerization from the cis-configuration to the trans-configuration is reversible in the presence of UV light.

7. The siRNA of claim 4, wherein the one or more available hydrogen atoms in the ortho position on the phenyl rings is replaced with a halogen, optionally chlorine.

8. The siRNA of claim 7, wherein:
(a) the azobenzene or derivative thereof undergoes isomerization from the trans-configuration to the cis-configuration in the presence of green and/or red light, and/or
(b) the azobenzene or derivative thereof undergoes isomerization from the cis-configuration to the trans-configuration in the presence of blue and/or violet light.

9. The siRNA of claim 1, wherein the siRNA has higher RNA silencing activity when the azobenzene or derivative thereof is in the trans-configuration compared to the cis-configuration.

10. The siRNA of claim 1, wherein the siRNA is directed to an oncogene.

11. A method of activating and/or inactivating an siRNA molecule comprising:
(a) providing a chemically-modified siRNA wherein one or more nucleotides of a strand of the siRNA are replaced with a spacer comprising an azobenzene or a derivative thereof, and
(b) exposing the chemically-modified siRNA to light from a light source,
wherein the azobenzene or derivative thereof undergoes isomerization between the cis-configuration and the trans-configuration upon exposure to the light and wherein the chemically-modified siRNA has higher RNA silencing activity when the azobenzene or derivative thereof is in the trans-configuration compared to the cis-configuration.

12. The method of claim 11, wherein:
(a) the light is UV light and the azobenzene or derivative thereof undergoes isomerization from the trans-configuration to the cis-configuration upon exposure to the UV light,
(b) the light is visible light and the azobenzene or derivative thereof undergoes isomerization from the cis-configuration to the trans-configuration upon exposure to the visible light,
(c) the light is green and/or red light and the azobenzene or derivative thereof undergoes isomerization from the trans-configuration to the cis-configuration upon exposure to the green and/or red light, and/or
(d) the light is blue and/or violet light and the azobenzene or derivative thereof undergoes isomerization from the cis-configuration to the trans-configuration upon exposure to the blue and/or violet light.

13. The method of claim 11, further comprising introducing the chemically-modified siRNA to a cell, optionally a bacterial cell, a fungal cell, a plant cell or a mammalian cell.

14. The method of claim 13, wherein the chemically-modified siRNA is exposed to the light source prior or after to introducing the siRNA to the cell.

15. The method of claim 11, further comprising:
(a) treating a disease associated with increased or aberrant expression of a gene, comprising administering the chemically-modified siRNA to a mammal or cell in need thereof, wherein the chemically-modified siRNA is directed to the gene, or
(b) treating cancer, comprising administering the chemically-modified siRNA to a mammal or cell in need thereof, wherein the siRNA is directed to an oncogene.

16. A method of reversibly silencing gene expression comprising:
(a) providing a cell with a chemically-modified siRNA directed to a gene in the cell, wherein one or more nucleotides of a strand of the siRNA are replaced with a spacer comprising an azobenzene or a derivative thereof, and
(b) exposing the cell to light from a light source that modulates the cis-trans isomerism of the azobenzene or derivative thereof.

17. The method of claim 16, wherein expression of the gene is decreased when the azobenzene or derivative thereof is in the trans-configuration.

18. The method of claim 17, wherein expression of the gene is lower when the azobenzene or derivative thereof is in the trans-configuration compared to the cis-configuration.

19. The method of claim 16, wherein the azobenzene or derivative thereof undergoes isomerization from the cis-configuration to the trans-configuration upon exposure to visible light or upon exposure to green and/or red light.

20. The method of claim 16, wherein the azobenzene or derivative thereof undergoes isomerization from the trans-configuration to the cis-configuration upon exposure to UV light or under exposure to blue and/or violet light.

* * * * *

UNITED STATES PATENT AND TRADEMARK OFFICE
CERTIFICATE OF CORRECTION

PATENT NO.        : 10,724,036 B2
APPLICATION NO.   : 15/992707
DATED             : July 28, 2020
INVENTOR(S)       : Desaulniers et al.

It is certified that error appears in the above-identified patent and that said Letters Patent is hereby corrected as shown below:

On the Title Page

Item (73), "Oshwa, Ontario (CA)" should read --Oshawa, Ontario (CA)--.

Signed and Sealed this
Twenty-second Day of December, 2020

Andrei Iancu
*Director of the United States Patent and Trademark Office*